United States Patent
Lee et al.

(10) Patent No.: US 10,443,033 B2
(45) Date of Patent: Oct. 15, 2019

(54) LACTOBACILLUS RHAMNOSUS RHT-3201 (KCTC 10833BP) CONJUGATED TO POLYSACCHARIDE POLYMER BINDER, AND USE THEREOF FOR PREVENTION OR TREATMENT OF ATOPIC DISEASES

(71) Applicant: IL DONG PHARMACEUTICAL CO., LTD., Seoul (KR)

(72) Inventors: Seung-Hun Lee, Gyeonggi-do (KR); Dae-Jung Kang, Gyeonggi-do (KR); Jae-Hoon Kang, Seoul (KR)

(73) Assignee: IL DONG PHARMACEUTICAL CO., LTD. (KR)

( * ) Notice: Subject to any disclaimer, the term of this patent is extended or adjusted under 35 U.S.C. 154(b) by 35 days.

(21) Appl. No.: 15/344,958

(22) Filed: Nov. 7, 2016

(65) Prior Publication Data
US 2017/0051247 A1 Feb. 23, 2017

Related U.S. Application Data

(63) Continuation of application No. PCT/KR2015/003914, filed on Apr. 20, 2015.

(30) Foreign Application Priority Data

May 7, 2014 (KR) .................. 10-2014-0054237

(51) Int. Cl.
| | | |
|---|---|---|
| *C12N 1/20* | (2006.01) | |
| *A61K 35/74* | (2015.01) | |
| *A23L 33/00* | (2016.01) | |
| *A23L 33/10* | (2016.01) | |
| *A23L 2/52* | (2006.01) | |

(52) U.S. Cl.
CPC .................. *C12N 1/20* (2013.01); *A23L 2/52* (2013.01); *A23L 33/00* (2016.08); *A23L 33/10* (2016.08); *A61K 35/74* (2013.01); *A23V 2002/00* (2013.01); *A23Y 2220/73* (2013.01)

(58) Field of Classification Search
None
See application file for complete search history.

(56) References Cited

U.S. PATENT DOCUMENTS 7,510,734 B2 * 3/2009 Sullivan .................. A61K 8/99
424/780
8,192,978 B2 * 6/2012 Kaesler .................. A23G 3/366
424/93.45

FOREIGN PATENT DOCUMENTS

| KR | 100742900 | * | 7/2007 |
| KR | 100742900 B1 | | 7/2007 |
| KR | 101166798 B1 | | 7/2012 |
| WO | 2011035093 A1 | | 3/2011 |
| WO | 2011114645 A1 | | 9/2011 |

OTHER PUBLICATIONS

Nan Li et al. Pediatric Research. 2009, vol. 66, No. 2, pp. 203-207.*
Schlesinger et al. "Efficacy and Safety of a Low-Molecular Weight Hyaluronic Acid Topical Gel in the Treatment of Facial Seborrheic Dermatitis", J Clin Aesthet Dermatol., 2012, vol. 5, No. 10, pp. 20-23.*

* cited by examiner

*Primary Examiner* — Vera Afremova
(74) *Attorney, Agent, or Firm* — Levenfeld Pearlstein, LLC

(57) ABSTRACT

The present invention relates to heat-killed *Lactobacillus rhamnosus* conjugated to a polysaccharide polymer binder, a preparation method therefor and a use thereof. The heat-killed *Lactobacillus rhamnosus* conjugated to a polysaccharide polymer binder of the present invention has an excellent therapeutic effect for atopic diseases, and particularly has high industrial applicability because membrane adhesion competitiveness, which is an advantage of existing lactic acid bacteria, is significantly improved, thereby exhibiting dermatitis preventing, alleviating and treating effects of the same level as steroid-based drugs.

8 Claims, 26 Drawing Sheets

LACTOBACILLUS RHAMNOSUS RHT-3201 (KCTC 10833BP) CONJUGATED TO POLYSACCHARIDE POLYMER BINDER, AND USE THEREOF FOR PREVENTION OR TREATMENT OF ATOPIC DISEASES

CROSS-REFERENCE TO RELATED APPLICATIONS

This is a Continuation of PCT Application No. PCT/KR2015/003914, filed Apr. 20, 2015, which claims the benefit of Korean Application No. 10-2014-0054237, filed May 7, 2014, the contents of which are incorporated fully by reference herein.

The present invention relates to heat-killed *Lactobacillus rhamnosus* conjugated to a polymeric polysaccharide binder, a preparation method therefor, and a use thereof and, more specifically, to a method for preparing heat-killed *Lactobacillus rhamnosus* conjugated to a polymeric polysaccharide binder, heat-killed *Lactobacillus rhamnosus* conjugated to a polymeric polysaccharide binder prepared by the method, and a pharmaceutical composition and a food composition for preventing and treating atopic dermatitis containing the heat-killed *Lactobacillus rhamnosus* conjugated to a polymeric polysaccharide binder as an active ingredient.

BACKGROUND ART

Atopic dermatitis (AD) refers to chronic and recurrent inflammatory skin manifestation showing pruritus, and is mainly observed in infants and children. Atopy is the most representative allergic disease together with allergic rhinitis and bronchial asthma, while it has been known that the atopy prevalence rate is 10-30% in children and 1-3% in adults.

Atopic dermatitis occurs due to a hypersensitive reaction of the immune system against antigens, such as dust mites, invading the body. The antigens are delivered to T cells through macrophages, while the T cells differentiate into Th1 or Th2 cells according to the type of antigens or receptors reacting therewith. Th2 cells activate humoral immunity through cytokines, such as IL-4, IL-5, and IL-10, and activate B cells, leading to increased IgE production and thus causing atopic dermatitis. Whereas, Th1 cells activate cellular immunity through IL-12 and IFN-γ, and IFN-γ inhibits the production of IgE. Therefore, the balance of the immune regulation of Th1 cells and Th2 cells is maintained to relieve atopic symptoms.

Although there is still no definitive treatment method for atopic dermatitis, anti-allergic drugs, anti-histaminic drugs, steroids, and other medicines are used therefor. Of these, steroids, which have been the most frequently prescribed one in an ointment formulation for treating atopic dermatitis, degrade immune responsiveness to reduce inflammation, while being reported to cause various types of side effects upon their long-term use.

Meanwhile, many lactic acid bacteria or dairy products containing lactic acid bacteria are being marketed as food materials having an immune regulatory action. Examples of the lactic acid bacteria may include *Lactobacillus genus, Lactococcus genus, Streptococcus genus, Pediococcus genus, Enterococcus genus*, and the like, and these lactic acid bacteria are known to have immunopotentiating or anti-allergic action. The present inventors were granted a patent right for *Lactobacillus rhamnosus* IDCC 3201 having a balanced immunoregulatory function of Th1 and Th2 cells, which is a novel strain material having no side effect upon being used for a long period of time and is capable of treating atopic dermatitis fundamentally (Korean Patent Registration No. 1007429000000).

However, 100 trillion or more enteric bacteria of approximately 500 different types are living in the human intestines, while harmful bacteria, such as *E. coli*, and beneficial bacteria, such as lactic acid bacteria, are maintained in a balanced manner as resident flora. Therefore, the administered lactic acid probiotics possess a limited capacity in their competitive adherence to the intestinal mucosa, and thus the effect thereof has been varied depending on their adhesion rate. In addition, certain number of lactic acid probiotic bacteria are killed during their passage of the gastrointestinal tract or dropped out of the adhesion competition and then are discharged together with defecation. Thus, the lactic acid probiotic bacteria have a limitation in their contribution to the treatment of severe atopy.

Moreover, probiotics need to be taken in a more excessive administrative manner than their standard counts so as to improve the efficiency of their adhesion to the intestinal mucosa, while being required to pass many obstacles in the body prior to their arrival at the intestines. Thus, the microbial intake count and the treatment efficiency of atopy are difficult to predict. Due to these problems, there are few lactic acid bacteria that exhibit the same level or treatment efficiency as steroid-based drugs. Despite efforts to improve the efficacy of probiotics in a composite formulation, there have been problems in that the normalized level for the effect of probiotics is unable to be established since the death of probiotic bacteria strains naturally occurs over time during their storage.

As studies about the human intestinal mucosal immune system have been recently progressed, there have been reports about the interaction and adhesive strength between intestinal mucosal immune cells of a human being as a host and cellular wall components of lactic acid bacteria. Of these, toll-like receptor-2 (TLR-2) of dendritic cells (DC) binds with lipoteichoic acid and peptidoglycan existing in the cellular wall of said bacteria to deliver immune-related signals.

In addition, the lactic acid bacteria having immunoregulatory functions achieve extracellular production of short chain fatty acid (SCFA) and immuno proteins when fermented in specific and distinct media, thereby promoting the secretion of IFN-γ and IL-12 from Th1 cells and thus leading to the alleviation of atopic dermatitis. However, while most products fermented with lactic acid bacteria do not alleviate atopic dermatitis, only some selective lactic acid bacteria produce these substances, and thus the value of developing such bacteria is high.

Under these backgrounds, the development of a composition is required that is useful to treat atopic dermatitis more fundamentally by overcoming the side effects of steroid-based drugs used for atopic dermatitis and the limitation of the lactic acid probiotics in the treatment of atopic dermatitis due to their adhesion rate.

DETAILED DESCRIPTION OF THE INVENTION

Technical Problem

The present inventors, during research to develop an atopic dermatitis treatment material having no side effects while maintaining a high efficacy at an equivalent level to steroid-based drugs, have verified that a conjugate of heat-killed *Lactobacillus rhamnosus* and a binder prepared by mixing a polymeric polysaccharide with a culture filtrate has excellent adhesive ability to intestinal mucosal immune cells and has a therapeutic efficacy for severe atopic dermatitis without side effects, and have completed the present invention.

Therefore, an aspect of the present invention is to provide a method for preparing heat-killed *Lactobacillus rhamnosus* conjugated to a polymeric polysaccharide binder, the method comprising: (a) separating a fermentation culture medium prepared by culturing *Lactobacillus rhamnosus* into bacteria and a fermentation filtrate; (b) mixing the fermentation filtrate in step (a) and a polymeric polysaccharide to prepare a polymeric polysaccharide binder; (c) heat-killing the bacteria separated in step (a); and (d) conjugating the heat-killed bacteria in step (c) to the binder prepared in step (b).

Another aspect of the present invention is to provide heat-killed *Lactobacillus rhamnosus* conjugated to a polymeric polysaccharide binder, as prepared by the above method.

Still another aspect of the present invention is to provide a pharmaceutical composition for preventing and treating atopic dermatitis, the composition comprising, as an active ingredient, the heat-killed *Lactobacillus rhamnosus* conjugated to a polymeric polysaccharide binder Still another aspect of the present invention is to provide a use of heat-killed *Lactobacillus rhamnosus* conjugated to a polymeric polysaccharide binder for preparing an agent for treating atopic dermatitis.

Still another aspect of the present invention is to provide a method for preventing or treating atopy, the method comprising administering an effective amount of heat-killed *Lactobacillus rhamnosus* conjugated to a polymeric polysaccharide binder to a subject in need of the prevention or treatment of atopy.

Still another aspect of the present invention is to provide a food composition for preventing and alleviating atopic dermatitis, the composition comprising, as an active ingredient, the heat-killed *Lactobacillus rhamnosus* conjugated to a polymeric polysaccharide binder.

Still further another aspect of the present invention is to provide a use of heat-killed *Lactobacillus rhamnosus* conjugated to a polymeric polysaccharide binder for preparing a food for preventing and alleviating atopic dermatitis.

Still another aspect of the present invention is to provide a method for preventing or alleviating atopy, the method comprising feeding a food comprising, as an active ingredient, an effective amount of heat-killed *Lactobacillus rhamnosus* conjugated to a polymeric polysaccharide binder to a subject in need of the prevention or alleviation of atopy.

Technical Solution

In accordance with an aspect of the present invention, there is provided a method for preparing heat-killed *Lactobacillus rhamnosus* conjugated to a polymeric polysaccharide binder, the method comprising: (a) separating a fermentation culture medium prepared by culturing *Lactobacillus rhamnosus* into bacteria and a fermentation filtrate; (b) mixing the fermentation filtrate of step (a) and a polymeric polysaccharide to prepare a polymeric polysaccharide binder; (c) heat-killing the bacteria separated in step (a); and (d) conjugating the heat-killed bacteria in step (c) to the binder prepared in step (b).

In accordance with another aspect of the present invention, there is provided heat-killed *Lactobacillus rhamnosus* conjugated to a polymeric polysaccharide binder, as prepared by the above method.

In accordance with still another aspect of the present invention, there is provided a pharmaceutical composition for preventing and treating atopic dermatitis, the composition comprising, as an active ingredient, the heat-killed *Lactobacillus rhamnosus* conjugated to a polymeric polysaccharide binder In accordance with still another aspect of the present invention, there is provided a use of heat-killed *Lactobacillus rhamnosus* conjugated to a polymeric polysaccharide binder for preparing an agent for treating atopic dermatitis.

In accordance with still another aspect of the present invention, there is provided a method for preventing or treating atopy, the method comprising administering an effective amount of heat-killed *Lactobacillus rhamnosus* conjugated to a polymeric polysaccharide binder to a subject in need of the prevention or treatment of atopy.

In accordance with still another aspect of the present invention, there is provided a food composition for preventing or alleviating atopic dermatitis, the composition containing, as an active ingredient, the heat-killed *Lactobacillus rhamnosus* conjugated to a polymeric polysaccharide binder.

In accordance with still another aspect of the present invention, there is provided a use of heat-killed *Lactobacillus rhamnosus* conjugated to a polymeric polysaccharide binder for preparing a food for preventing and alleviating atopic dermatitis.

In accordance with still another aspect of the present invention, there is provided a method for preventing or alleviating atopy, the method comprising feeding a food comprising, as an active ingredient, an effective amount of heat-killed *Lactobacillus rhamnosus* conjugated to a polymeric polysaccharide binder to a subject in need of the prevention or alleviation of atopy.

Hereinafter, the present invention will be described in detail.

The present invention provides a method for preparing heat-killed *Lactobacillus rhamnosus* conjugated to a polymeric polysaccharide binder, the method comprising:

(a) separating a fermentation culture medium prepared by culturing *Lactobacillus rhamnosus* into bacteria and a fermentation filtrate;

(b) mixing the fermentation filtrate of step (a) and a polymeric polysaccharide to prepare a polymeric polysaccharide binder;

(c) heat-killing the bacteria separated in step (a); and (d) conjugating the heat-killed bacteria in step (c) to the binder prepared in step (b).

Step (a) is a Process of Separating a Fermentation Culture Medium, which is a *Lactobacillus Rhamnosus* Cultured Product, into Bacteria and a Fermentation Filtrate.

The *Lactobacillus rhamnosus* lactic acid bacteria of the present invention include all of *Lactobacillus rhamnosus* strains, and may preferably be *Lactobacillus rhamnosus* KCTC 10833 BP.

The *Lactobacillus rhamnosus* KCTC 10833 BP is named "*Lactobacillus rhamnosus* IDCC 3201" in the previous Korean patent application (No. 10-2006-0038066) by the present applicant, and herein, the names may be exchangeably used with each other.

As used herein, the term "culturing" has a meaning including fermentation. The culturing herein may be conducted by known methods for culturing lactic acid bacteria. Examples of the culturing may include, but are not limited to, a method wherein bacteria are inoculated in a culture medium or culture substrate, and then are left for a predetermined period of time while a predetermined growth temperature is maintained under aerobic or anaerobic conditions.

As used herein, the term "culture medium" refers to a solid or liquid culture substrate containing nutrients necessary for growing animal cells, plant cells, or microorganisms. Herein, the culture medium may include known culture media for lactic acid bacteria. Example of the culture medium may include, but are not limited to, a deMan Rogosa Sharpe (MRS) liquid medium, an All Purpose with Tween (APT) medium, and a Brain Heart Infusion (BHI) medium, and may preferably be an MRS liquid medium. The media may be used in the form of a modified medium (e.g., a modified MRS medium) by selectively adjusting the composition of materials and the contents of materials constituting the medium according to the desire of a person skilled in the art.

The culture medium of the present invention contains, as medium substrates, carbon sources, nitrogen sources, minerals, and growth elements necessary for the growth of lactic acid bacteria. The types of carbon sources, nitrogen sources, minerals, and growth elements are not limited as long as these materials stimulate a synergistic action for the growth of lactic acid bacteria, while these materials are known in the relevant fields. For instance, various carbohydrates may be used as the carbon source. The carbon source may preferably be glucose, sucrose, maltose, fructose, lactose, xylose, galactose, or arabinose. In addition, various organic nitrogen sources may be used as the nitrogen source. The nitrogen source may preferably be a yeast extract, soytone, peptone, a beef extract, tryptone, or casitone. The type of mineral source is not limited as long as the mineral source is known in the art for growing lactic acid bacteria. Examples of the mineral sources may include magnesium sulfate ($MgSO_4$), manganese sulfate ($MnSO_4$), dipotassium hydrogen phosphate ($K_2HPO_4$), ammonium chloride ($NH_4Cl$), calcium carbonate ($CaCO_3$), and sodium acetate ($CH_3COONa$). In addition, various raw food material powders or extracts may be optionally added to the culture medium according to the need of a person skilled in the art, while examples thereof may include a corn powder or extract, a whey powder or extract, a skimmed milk powder or extract, a green tea powder or extract, or a mushroom powder or extract, but are not limited thereto.

In the culturing process, the temperature may be changed depending on the type of lactic acid bacteria by a person skilled in the art. For instance, the temperature may be 30-45° C., but is not limited thereto. The temperature may be preferably 33-40° C., and most preferably 35-39° C.

In the culturing process, the culturing time may be changed depending on a desired working efficiency by a person skilled in the art. For example, it may be 12-96 hours, but is not limited thereto.

As used herein, the term "fermentation culture medium" refers to one obtained by inoculating and fermenting (or culturing) a strain in a liquid medium, while the term "fermentation filtrate" refers to a culture filtrate obtained by removing the strain from the fermented culture liquid.

The separation of the bacteria and the fermentation filtrate may be conducted by known bacteria separation methods (for example, centrifugation or ultrafiltration), but are not limited thereto.

Step (b) is a Process of Mixing the Fermentation Filtrate Separated in Step (a) with a Polymeric Polysaccharide Material to Prepare a Polymeric Polysaccharide Binder.

As used herein, the term "polymeric polysaccharide binder" refers to a mixture of a fermentation filtrate and a polymeric polysaccharide material, or a concentrate of the mixture. Depending on the composition and the preparation procedure of the binder, the adhesive ability to the intestinal mucosa and the ability to produce various cytokines in immune cells may be regulated.

The type of polymeric polysaccharide material in step (b) is not limited as long as the polymeric polysaccharide material is known in the art. Examples of the polymeric polysaccharide material may include hyaluronic acid, alginate, maltodextrin, chitosan, carrageenan, galactomannan, glucomannan, dextran, fucoidan, agar, porphyran, chitin, and the like. The polymeric polysaccharide of the present invention may be preferably hyaluronic acid, alginate, maltodextrin, or chitosan.

The percentage of the polymeric polysaccharide material added may be selectively changed depending on the viscosity or adhesive strength desired by a person skilled in the art. For example, the polymeric polysaccharide material may be added to the fermentation filtrate at a ratio of 0.0001-10% (w/v), but is not limited thereto.

Herein, a preferable embodiment of step (b) may include the addition of hyaluronic acid as a polymeric polysaccharide material to the fermentation filtrate at a ratio of 0.0001-10% (w/v), and most preferably the addition of hyaluronic acid to the fermentation filtrate at a ratio of 0.0001-0.01% (w/v).

The hyaluronic acid is one of the complex polysaccharides composed of amino acids and uronic acids, and is a polymer compound composed of N-acetylglucosamine and glucuronic acid. The molecular weight of the hyaluronic acid of the present invention is not limited. For example, the hyaluronic acid includes hyaluronic acids having a molecular weight of 1,000,000, 2,000,000, 3,000,000, 4,000,000, and 4,500,000, preferably hyaluronic acid having a molecular weight of 1,000,000 or 2,000,000, and most preferably hyaluronic acid having a molecular weight of 1,000,000.

Step (b) may further include a concentration process to obtain a highly concentrated polymeric polysaccharide binder.

The concentration as used herein may be conducted by concentrating devices or methods known in the art. Examples of the concentration may include, without being limited thereto, precipitation concentration, evaporation concentration, concentration under reduced pressure, ultrafiltration, reverse osmosis, and centrifugation, preferably concentration under reduced pressure.

Step (c) is a Process of Heat-Killing the Bacteria Separated in Step (a).

The term "heat-killing" refers to killing probiotic bacteria through heat treatment for a predetermined period of time, while the heat-killing affects the composition of active ingredients contained in bacteria, the structure of bacteria, and adhesive ability to the intestines depending on the heat-killing condition. The most important purpose of heat-killing probiotic bacteria is to form a structure that favorably adheres to intestinal mucosal immune cells by inducing lipoteichoic acid and peptidoglycan, which are representative ingredients contained in the cell structure of *Lactobacillus rhamnosus*. That is, the lipoteichoic acid and peptidoglycan forming the cell structure are combined with TRL-2 of dendritic cells of the intestinal mucosa to promote the production of immune-related cytokines, and thus it is important that the structure is prepared in such a form as to have the most favorable adhesion efficiency.

The temperature for the heat-killing in the present invention is not limited as long as it is within a temperature range in which functional ingredients of bacteria are not denatured.

The temperature may be, for example, 60-100° C., preferably 70-90° C., and most preferably 75-85° C.

The time for the heat-killing is not limited as long as it is within a time range in which functional ingredients of bacteria are not denatured. The time may be, for example, 10-120 minutes, preferably 30-90 minutes, and most preferably 50-70 minutes.

After the heat-killing process, a cooling process may be optionally added according to the need of a person skilled in the art. The cooling process may be conducted by known cooling methods, and the cooling temperature may be selectively changed according to the desire of a person skilled in the art. The cooling process may be conducted at a temperature range of, for example, 10-40° C., and preferably 25-35° C.

Step (d) is a Process of Conjugating the Heat-Killed Bacteria in Step (c) to the Binder Prepared in Step (b).

The term "conjugating" refers to forming a single unit by coupling two or more materials. In step (d), the binder and the heat-killed bacteria are conjugated by a series of reactions induced by infiltrating the heat-killed bacteria of step (c) into the binder prepared in step (b) or mixing the heat-killed bacteria and the binder.

The preparation method comprising steps (a) to (d) may optionally further include an excipient-adding process, a drying process, and a pulverizing process in order to facilitate handling, storage, and the like at the time of preparing heat-killed *Lactobacillus rhamnosus* conjugated to a polymeric polysaccharide binder, in accordance with the need of a person skilled in the art.

The type of excipient is not limited as long as it is known in the art. Examples of the excipient may include starch.

The drying process may be conducted by known drying methods. Examples of the drying process may include freeze-drying, spray drying, and hot-air drying, but are not limited thereto.

The present invention provides the heat-killed *Lactobacillus rhamnosus* conjugated to a polymeric polysaccharide binder prepared by the above method.

The heat-killed *Lactobacillus rhamnosus* conjugated to a polymeric polysaccharide binder according to the present invention is characterized by being prepared by the method comprising steps (a) to (d). The heat-killed *Lactobacillus rhamnosus* conjugated to a polymeric polysaccharide binder is named "RHT-3201" by the present inventors, and herein, the terms may be exchangeably used with each other.

The heat-killed *Lactobacillus rhamnosus* conjugated to a polymeric polysaccharide binder according to the present invention is shown to possess an excellent therapeutic effect of treating atopic disease, together with a significantly improved adhesive competitiveness to the intestinal mucosa compared to existing lactic acid bacteria preparations (see Example 6), and the effects of preventing, alleviating, or treating atopic dermatitis at an equivalent level to existing steroid-based drugs (e.g., dexamethasone) (see Examples 9 and 10).

In addition, with respect to the stability in the gastrointestinal tract environment, which is problematic upon the oral intake of lactic acid probiotics, the heat-killed *Lactobacillus rhamnosus* conjugated to a polymeric polysaccharide binder according to the present invention maintains its functionalities (effectiveness) at a higher level than the conventional lactic acid probiotics. More particularly, in spite of the exposure to artificial gastric fluid (gastric acids) and artificial intestinal fluid (bile acids), the heat-killed *Lactobacillus rhamnosus* conjugated to a polymeric polysaccharide binder according to the present invention maintains its adhesion efficiency to the intestinal mucosa at a high level (see Example 7), while its storage stability at various temperatures was also confirmed (see Example 8).

As used herein, "atopy" refers to a series of allergic symptoms shown on the skin, respiratory mucosa, ocular mucosa, intestinal mucosa or the like in an individual having atopic tendency, and such atopic tendency (predisposition) is passed down to exhibit family characteristics. Allergic diseases caused by atopic tendency may include allergic dermatitis, allergic rhinitis, asthma, allergic conjunctivitis, atopic hives, and the like, and these diseases may occur alone or several diseases may occur at the same time. Atopic dermatitis, which is one of representative skin diseases shown in persons having atopic allergies, is a chronic skin disease, often, called congenital fever. Atopic dermatitis has dry skin and pruritus as main symptoms, while in some cases being accompanied by other allergic diseases (such as hives, metal allergies, asthma, and allergic rhinitis) through its immunological characteristics and family tendency.

As used herein, "atopic dermatitis (AD)" is a chronic and recurrent inflammatory skin condition with pruritus, and shows a hypersensitive reaction of the immune system against antigens, such as dust mites, invading the body. The antigens invading the body are delivered to T cells through macrophages, while T cells differentiate into Th1 or Th2 cells depending on the type of antigens or receptor reacting therewith. Th2 cells then activate humoral immunity through cytokines, such as IL-4, IL-5, and IL-10, and activate B cells, leading to increased IgE production and then causing atopic dermatitis. That is, as for the immune abnormality in atopic dermatitis, while immunoglobulin IgE adheres to surfaces of mast cells around the blood vessels in the body or in the skin, antigens again invade the human body to bind with immunoglobulins to activate the mast cells, thereby allowing the mast cells to secrete chemical substances such as histamine. These chemical substances stimulate the blood vessels and the skin, causing red spots, edema, and pruritus on the skin, thereby causing or aggravating atopic dermatitis.

On the contrary, Th1 cells activate cellular immunity through IL-12 and IFN-γ, while IFN-γ inhibits the production of IgE.

Therefore, considering that the balanced immune regulation of Th1 cells and Th2 cells is an essential key in the prevention or treatment of atopic symptoms, the heat-killed *Lactobacillus rhamnosus* conjugated to a polymeric polysaccharide binder according to the present invention is found to be excellent in the balanced immune regulation of Th1 and Th2 cells, especially achieving a balanced immune regulation between Th1 type cytokines and Th2 type cytokines through different immunoregulatory mechanisms according to the severity of atopic dermatitis (see Examples 9 and 10). That is, in the case of mild atopic dermatitis, the heat-killed *Lactobacillus rhamnosus* conjugated to a polymeric polysaccharide binder according to the present invention regulates and maintains the immunological balance of Th1 and Th2 cells, while in the case of severe atopic dermatitis, it inhibits activities of Th1 and Th2 cells through the stimulation of regulatory T cells, thereby treating and alleviating severe atopic dermatitis.

Therefore, the present invention provides a pharmaceutical composition for preventing and treating atopic dermatitis, the composition comprising, as an active ingredient, the heat-killed *Lactobacillus rhamnosus* conjugated to a polymeric polysaccharide binder. Furthermore, the present invention provides: a use of heat-killed *Lactobacillus rhamnosus* conjugated to a polymeric polysaccharide binder for preparing an agent for treating atopic dermatitis; and a method for treating or preventing atopy, the method comprising administering an effective amount of heat-killed *Lactobacillus rhamnosus* conjugated to a polymeric polysaccharide binder to a subject in need of the treatment or prevention of atopy.

The atopic dermatitis as described in the present invention is classified into mild, moderate, and severe types depending on the progression of disease symptoms. The atopic dermatitis in the present invention may be preferably severe atopic dermatitis.

As used herein, the term "subject" may be an animal, preferably a mammal, and particularly, an animal including a human being.

There have been many reports with respect to scales for assessing clinical courses and therapeutic efficacy of atopic dermatitis. As the representative scale, Eczema Area and Severity Index (EASI), SCORing Atopic Dermatitis (SCORAD), Patient Oriented Eczema Measure (POEM), and Three Item Severity (TIS) are known. Preferably, the severity of the atopic dermatitis in the present invention is classified according to SCORing Atopic Dermatitis (SCORAD).

The pharmaceutical composition according to the present invention may contain a pharmaceutically effective amount of the heat-killed *Lactobacillus rhamnosus* conjugated to a polymeric polysaccharide binder alone or may further contain at least one pharmaceutically acceptable carrier. The pharmaceutical composition of the present invention may be administered to a patient in a single dose, or may be administered in a multiple dose by fractionated treatment protocol for a long period of time. As used herein, the term "pharmaceutically effective amount" refers to an amount required to exhibit a higher response compared with a negative control, and preferably an amount sufficient to treat or prevent atopic dermatitis. The effective amount of the heat-killed *Lactobacillus rhamnosus* conjugated to a polymeric polysaccharide binder according to the present invention may be 0.001-1000 mg/kg b.w./day, and preferably 0.055-16.65 mg/kg b.w./day, but is not limited thereto. However, the pharmaceutically effective amount may be appropriately varied depending on various factors, such as the type of the disease and severity thereof, age, body weight, physical condition, and gender of a patient, the administration route, and treatment period.

The composition of the present invention may be variously formulated together with the pharmaceutically acceptable carrier, depending on a route of administration, by methods known in the art. As used herein, the term "pharmaceutically acceptable" composition refers to a non-toxic composition that is physiologically acceptable, does not inhibit the action of an active ingredient when administered to humans, and does not usually induce an allergic reaction or similar reactions, such as gastroenteric troubles and dizziness. The composition of the present invention may be variously formulated, together with the pharmaceutically acceptable carrier, depending on a route of administration, by a method known in the art. The route of administration may be, but is not limited to, oral or parenteral administration, and preferably oral administration.

The pharmaceutical composition of the present invention, when orally administered, may be formulated, together with a suitable carrier for oral administration, in the form of a powder, granules, a tablet, a pill, a sugar coated tablet, a capsule, a liquid, a gel, a syrup, a suspension, a wafer, or the like by methods known in the art. For example, the tablet or sugar coated tablet for an oral preparation may be obtained by mixing an active ingredient with a solid excipient, pulverizing the mixture, adding a suitable adjuvant thereto, and then processing the mixture into a granule mixture. Examples of the suitable excipient may include: sugars including lactose, dextrose, sucrose, sorbitol, mannitol, xylitol, erythritol, and maltitol; starches including corn starch, wheat starch, rice starch, and potato starch; celluloses including cellulose, methyl cellulose, sodium carboxy methyl cellulose, and hydroxypropyl methyl cellulose; and a filler, such as gelatin or polyvinyl pyrrolidone. In some cases, cross-linked polyvinyl pyrrolidone, agar, alginic acid, or sodium alginate may be added as a disintegrant. Further, the pharmaceutical composition of the present invention may further contain an anti-coagulant, a lubricant agent, a wetting agent, a favoring agent, an emulsifier, and a preservative.

In addition, when parenterally administered, the pharmaceutical composition according to the present invention, together with a suitable carrier for parenteral administration, may be formulated by methods known in the art. For other pharmaceutically acceptable carriers, ones disclosed in the following literature may be referred (Remington's Pharmaceutical Sciences, 19th ed., 1995, Mack Publishing Company, Easton, Pa.).

Furthermore, the pharmaceutical composition according to the present invention may be administered together with compounds known to be effective in preventing and treating atopic diseases or atopic dermatitis.

In addition, the present invention provides a food composition for preventing and alleviating atopic dermatitis, the composition comprising, as an active ingredient, the heat-killed *Lactobacillus rhamnosus* conjugated to a polymeric polysaccharide binder. In addition, the present invention provides: a use of heat-killed *Lactobacillus rhamnosus* conjugated to a polymeric polysaccharide binder for preparing a food for preventing and alleviating atopic dermatitis; and a method for preventing or alleviating atopy by feeding a food comprising, as an active ingredient, heat-killed *Lactobacillus rhamnosus* conjugated to a polymeric polysaccharide binder to a subject in need of the prevention or alleviation of atopy As used herein, the term "subject" may be an animal, preferably a mammal, and particularly, an animal including a human being.

The food composition of the present invention includes all types including functional food, nutritional supplements, health food, food additives, yogurt drink, and fermented milk. The above types of food compositions may be prepared in various forms by general methods known in the art. Preferably, the food of the present invention may be fermented milk, yogurt, beverage, milk beverage, food additives, and health functional food.

For example, for the health food, the heat-killed *Lactobacillus rhamnosus* conjugated to a polymeric polysaccharide binder according to the present invention may be prepared, for drinking, into a form of yogurt beverage, fermented milk, tea, juice, and drink, or may be granulated, capsulated, or powdered, for intake. In addition, the heat-killed *Lactobacillus rhamnosus* conjugated to a polymeric polysaccharide binder according to the present invention may be mixed with a known material or an active ingredient, which is known to be effective in alleviating atopic diseases (specifically, atopic dermatitis), to be prepared in the form of a composition.

Also, for the functional food, the heat-killed *Lactobacillus rhamnosus* conjugated to a polymeric polysaccharide binder according to the present invention may be added to drinks (including alcoholic drinks), fruits and processed products thereof (e.g., canned fruit, bottled fruit, jam, marmalade), fish, meat and processed products thereof (e.g., ham, sausage, corned beef), confectionery and noodles (e.g., udon, buckwheat noodles, ramen, spaghetti, macaroni), fruit juice, drinks, cookies, taffy, dairy products (e.g., butter, cheese), vegetable oils, margarine, vegetable proteins, retort foods, frozen foods, various seasonings (e.g., soybean paste, soy sauce, sauce), or the like.

In the food composition of the present invention, the content of the heat-killed *Lactobacillus rhamnosus* conjugated to a polymeric polysaccharide binder is preferably, 0.001-50 wt % of the finally prepared food, but is not limited thereto.

In addition, in order to use the heat-killed *Lactobacillus rhamnosus* conjugated to a polymeric polysaccharide binder in the form of a food additive, the heat-killed *Lactobacillus rhamnosus* conjugated to a polymeric polysaccharide binder according to the present invention may be prepared in the form of a powder or a concentrated liquid.

In the pharmaceutical and food compositions according to the present invention, the amount of the active ingredient mixed may be suitably determined according to the purpose of their use (prevention, health, or symptom alleviation), and for example, the heat-killed *Lactobacillus rhamnosus* conjugated to a polymeric polysaccharide binder may be contained at a concentration of $10^8$-$10^{10}$ CFU/g. The effective dose of the heat-killed *Lactobacillus rhamnosus* conjugated to a polymeric polysaccharide binder according to the present invention may be determined according to the above concentration range, but may be less than the above described range for the purpose of health and hygiene or for a long-term intake for health control. The active ingredient has no problem in view of safety, and may thus be used in an excessive amount higher than the above described range.

Advantageous Effects

The heat-killed *Lactobacillus rhamnosus* conjugated to a polymeric polysaccharide binder according to the present invention is excellent in treating atopic disease, significantly improves the adhesive competitiveness to the intestinal mucosa compared to existing lactic acid bacteria preparations, and exhibits an effect of preventing, alleviating, or treating atopic dermatitis at an equivalent level to existing steroid-based drugs. In addition, the heat-killed *Lactobacillus rhamnosus* conjugated to a polymeric polysaccharide binder according to the present invention is excellent in the balanced immune regulation of Th1 and Th2 cells, and especially achieves balanced immune regulation between Th1 type cytokines and Th2 type cytokines through different immunoregulatory mechanisms according to the severity of atopic dermatitis.

MODE FOR CARRYING OUT THE INVENTION

Figure 1:
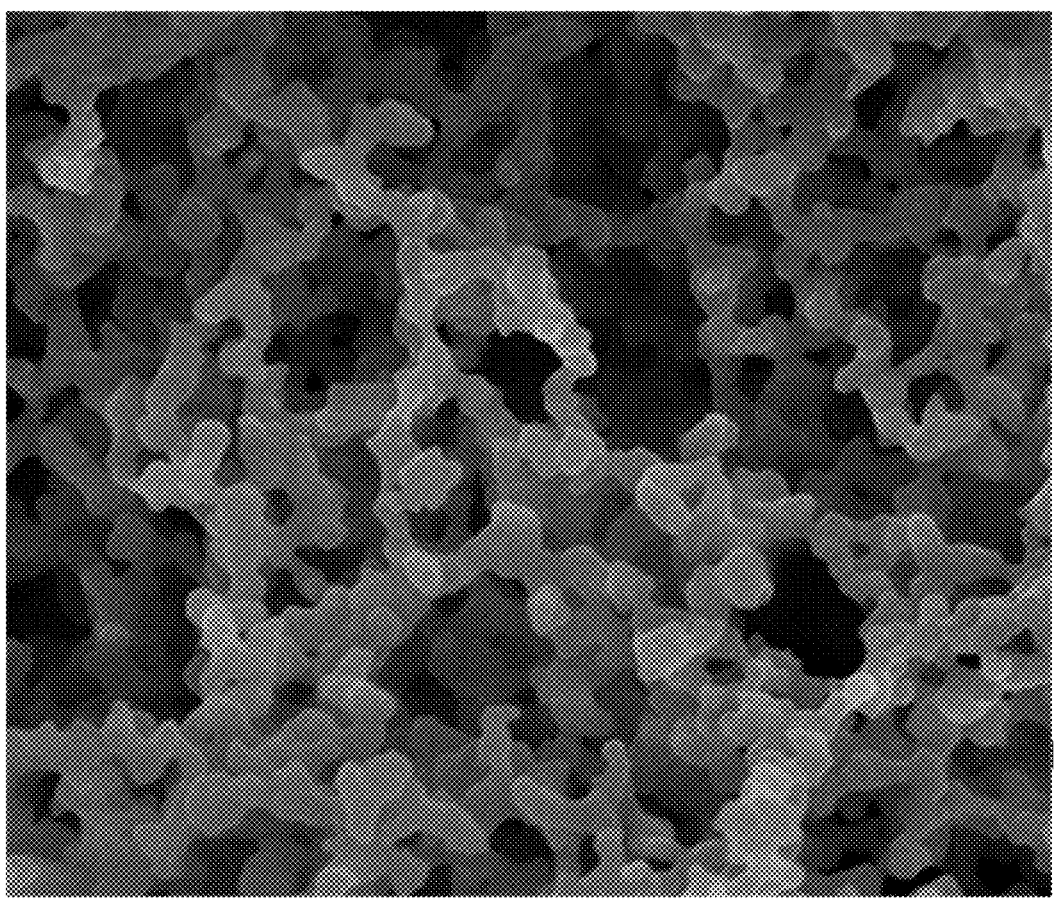
FIG. 1 is an electron microscopic image showing a structure of hyaluronic acid.

Hereinafter, the present invention will be described in detail.

However, the following examples are merely for illustrating the present invention and are not intended to limit the scope of the present invention.

Example 1

Evaluation on Effects of Binders by Type

<1-1> Preparation of Various Types of Binder Samples

*Lactobacillus rhamnosus* IDCC 3201 (KCTC 10833BP) were cultured in MRS medium containing 0.1-1% whey powder at 37° C. for 24 hours. After culturing, bacteria and a culture filtrate were separated via centrifugation. Then, hyaluronic acid, alginate, maltodextrin, chitosan, and polyethylene glycol were added at 0.1% (w/v) to the culture filtrate, respectively, followed by stirring for 1 hour and then concentration, thereby preparing binders which were then freeze-dried. Each sample was diluted with a phosphate buffer solution to prepare a final 1 μg/ml of sample. Skimmed milk powder was used as a control.

<1-2> Preparation of Spleen Cells 5-week old female BALB/c mice were boosted with 2 mg of aluminum hydroxide and 1 mg of ovalbumin through intraperitoneal injection, and second-boosted in the same manner after six days. On day 13, the spleen was harvested from each mouse and spleen cells were extracted, thereby preparing spleen cell liquid. Preferably, the spleen cells were prepared by the following method.

The mouse spleen was aseptically harvested, and 10 ml of Hanks' balanced salt solution (HBSS) was dropwise added. It was burst using tweezers on a 60-mesh net to collect a cell suspension, and then allowed to overlap 2.5 ml of fetal bovine serum, followed by standing for 10 minutes, thereby precipitating large masses. The large masses were suspended in an $NH_4Cl$ solution (pH 7.0) for 3-4 minutes to achieve the hemolysis of red blood cells. Then, the suspension was mixed with 2.5 ml of fetal bovine serum, followed by centrifugation at 1,500 RPM for 5 minutes. The precipitate was washed twice with HBSS, and then dispensed in DMEM medium containing 10% fetal bovine serum and 1 mg/ml ovalbumin at $5 \times 10^6$ cells/ml, thereby preparing spleen cells.

<1-3> Culture of Spleen Cells and Measurement of Cytokines

200 μl of spleen cell suspension ($5 \times 10^6$ cells/ml) and 10 μl (1 μg/ml) of each sample liquid prepared in <1-1> were added to each well of a 96-well plate, followed by culturing in a 5% $CO_2$ incubator for 7 days. After the completion of the culture, IL-4 and IL-12 levels in the culture liquid were measured using the Cytoset kit (Biosource). The levels of IL-4 and IL-12 production by each sample were expressed as a rate of increase compared with the control as shown in Table 1.

TABLE 1

Determination of binders

| Type of Binder | Increase (%) compared with control | | IL-4/IL-12 ratio |
|---|---|---|---|
| | IL-4 | IL-12 | |
| Hyaluronic acid | 5 | 52 | 0.09 |
| Alginate | 15 | 29 | 0.51 |
| Maltodextrin | 9 | 36 | 0.25 |
| Chitosan | 17 | 38 | 0.44 |
| Polyethylene glycol | 13 | 22 | 0.59 |

As test results, the hyaluronic acid binder showed a 5% increase in IL-4 production and a 52% increase in IL-12 production. The alginate binder showed a 15% increase in IL-4 production and a 29% increase in IL-12 production. The maltodextrin binder showed a 9% increase in IL-4 production and a 36% increase in IL-12 production. The chitosan binder showed a 17% increase in IL-4 production and a 38% increase in IL-12 production. The polyethylene glycol binder showed a 13% increase in IL-4 production and a 22% increase in IL-12 production. Therefore, when the binder was prepared using a polymeric polysaccharide, the increase rate of IL-12 was relatively high, while the increase rate of IL-4 was relatively low. Of these, the hyaluronic acid showed the highest increase rate of IL-12 and a relatively low increase rate of IL-4. Following hyaluronic acid, maltodextrin, chitosan, and alginate showed favorable results in that order.

Example 2

Evaluation on Effects of Binders by Concentration

<2-1> Preparation of Samples by Concentration

The effects of binders by concentration were evaluated while, among the polymeric polysaccharide materials, the hyaluronic acid showing the best effect in Example 1 was used as a representative material. The hyaluronic acid was added at an amount of 0.0001-1% (w/v) to the culture filtrate, followed by stirring for 1 hour, and then the mixture was concentrated under reduced pressure, thereby preparing hyaluronic acid binders with different concentrations, respectively, and these binders were freeze-dried. Each sample was diluted with a phosphate buffer to prepare a final 1 μg/ml of sample. Skimmed milk powder was used as a control.

<2-2> Test on Cytokine Production

The cytokine production rate in the spleen cells was investigated for the binder samples prepared in Example <2-1> by the same method as in Example <1-3>. The results are shown in Table 2 below.

TABLE 2

Determination of concentration of hyaluronic acid added

| Hyaluronic acid concentration (w/v) | Incease (%) compared with control | | IL-4/IL-12 ratio |
|---|---|---|---|
| | IL-4 | IL-12 | |
| 0.0001 | 9 | 46 | 0.19 |
| 0.001 | 7 | 52 | 0.13 |
| 0.01 | 10 | 37 | 0.27 |
| 0.1 | 12 | 33 | 0.36 |
| 1 | 15 | 25 | 0.60 |

As test results, as shown in Table 2 above, the optimal concentration of hyaluronic acid for preparing a hyaluronic acid binder was 0.001% (w/v), and here, the production of IL-4 was reduced compared with that in the control, and the production of IL-12 was increased compared with that in the control.

Example 3

Evaluation on Effects of Bacteria by Heat-Killing Condition

In order to determine the optimal bacteria heat-killing conditions, the heat-killing conditions according to the temperature and time were optimized and the adhesive ability to Caco-2 cells was evaluated, thereby selecting optimal conditions. More details for the test were as follows.

<3-1> Preparation of Heat-Killed Bacteria Samples

*Lactobacillus rhamnosus* bacteria were heat-killed at 60-120° C. for 10, 20, 30, 40, 50, and 60 minutes (Heater, EYELA OSB-2100, China), and cooled at 30° C. before being used as test samples. Each sample was washed twice with a phosphate buffer solution, re-suspended in a 1 ml of the same buffer solution, and diluted to $1 \times 10^8$ cells/ml in serum-free DMEM, before being used for the test.

<3-2> Evaluation on Adhesive Ability to Intestinal Mucosa

The Caco-2 cell monolayer was prepared by inoculating Caco-2 cells (Korean Cell Line Bank) at $1.2 \times 10^5$ cells/ml in Dulbecco's Modified Eagle's Medium (DMEM, Hyclone, USA) supplemented with 10% (v/v) fetal calf serum and 20 μl/ml gentamicin, dispensing 1 μml of the resultant medium in each well of the 6-well tissue culture plate, culturing the cells for 7 days, and washing twice with a phosphate buffer solution.

1 ml of the sample liquid prepared in Example <3-1> was put into each well in which the Caco-2 monolayer was formed, followed by reaction for 90 minutes. 1 ml of DMEM, instead of heat-killed lactic acid bacteria, was used as a control. After the reaction, the supernatant was removed, and 1 ml of 0.04% (w/v) Tween 80 was added to recover the heat-killed lactic acid bacteria adhering to the Caco-2 cells, and the bacterial count was measured using a hemocytometer. The adhesion efficiency was calculated as a ratio of the adhering bacterial count to the initial bacterial count (see Table 3).

TABLE 3

Adhesion rate according to heat-killing condition of bacteria

|  |  | Adhesion rate (%) to Caco-2 cells | | | |
| --- | --- | --- | --- | --- | --- |
|  |  | 60° C. | 70° C. | 80° C. | 90° C. |
| Heat killing time (minutes) | 10 | 44 | 50 | 56 | 45 |
|  | 20 | 48 | 53 | 68 | 49 |
|  | 30 | 56 | 63 | 71 | 54 |
|  | 40 | 60 | 66 | 76 | 42 |
|  | 50 | 62 | 71 | 80 | 35 |
|  | 60 | 63 | 72 | 85 | 32 |

As shown in Table 3, the adhesion efficiency was most favorable when the heat-killing conditions of 80° C. and 60 minutes were applied. The constituent elements, such as lipoteichoic acid, existing on the cellular wall of lactic acid bacteria, inhibit the adhesion of harmful bacteria, such as *E. coli* and *Salmonella*, to the intestinal mucosal surface, and bind with TLR-2, which is one of the receptors of dendritic cells among intestinal mucosal cells, to be involved in the activation of human intestinal tract immunity. Therefore, the optimal bacteria heat-killing conditions are established to facilitate the emission of related factors existing on the cellular wall, so that the heat-killed lactic acid bacteria are allowed to adhere to the intestinal tract while being in competition with resident flora of the intestinal tract, and thus, ultimately, the activation of the intestinal tract immunity can be expected.

Example 4

Preparation of Heat-Killed *Lactobacillus Rhamnosus* Conjugated to Polymeric Polysaccharide Binder The bacteria heat-killed at 80° C. for 60 minutes in Example 3 was mixed with 0.001% of the hyaluronic acid binder prepared in Example 2 in which the *Lactobacillus rhamnosus* culture filtrate was concentrated, followed by reaction. A carrier, such as starch, as a vehicle, was mixed with the resultant reaction material, followed by a drying process, thereby preparing heat-killed *Lactobacillus rhamnosus* conjugated to a polymeric polysaccharide binder (hereinafter, expressed by "RHT-3201"). The immunity promotion effect was relatively compared between RHT-3201 prepared as above and *Lactobacillus rhamnosus* IDCC 3201 as a probiotic, by the same method as in Example <1-3> (see Table 4).

TABLE 4

Comparison of immunity promotion effect between conventional probiotic bacterium and RHT-3201 according to the present invention

|  | RHT-3201 | Probiotic preparation |
| --- | --- | --- |
| IL-4 increase (%) compared with control | 3 | 20 |
| IL-12 increase (%) compared with control | 67 | 29 |
| IL-4/IL-12 ratio | 0.04 | 0.68 |

As shown in Table 4, it was verified that the regulating effect of cytokines involved in Th1/Th2 was 17-fold higher in RHT-3201 lactic acid bacteria of the present invention, compared with an existing probiotic. It is suggested that the RHT-3201 was prepared in such a form that it favorably binds to a corresponding receptor of the intestinal mucosa, such as TLR-2 during the preparing process.

Example 5

Structural Analysis Through Electron Microscope (FE-SEM)

As for the phase of RHT-3201 prepared in Example 4, structural analysis was conducted through photographing using an electron microscope (FE-SEM, Model: LEO SUPRA 55, GENESIS 2000 (Carl Zeiss, EDAX)) according to each preparation process. The structural analysis results using the electron microscope according to the RHT-3201 preparation steps are shown in FIGS. 1 to 5.

Figure 2:
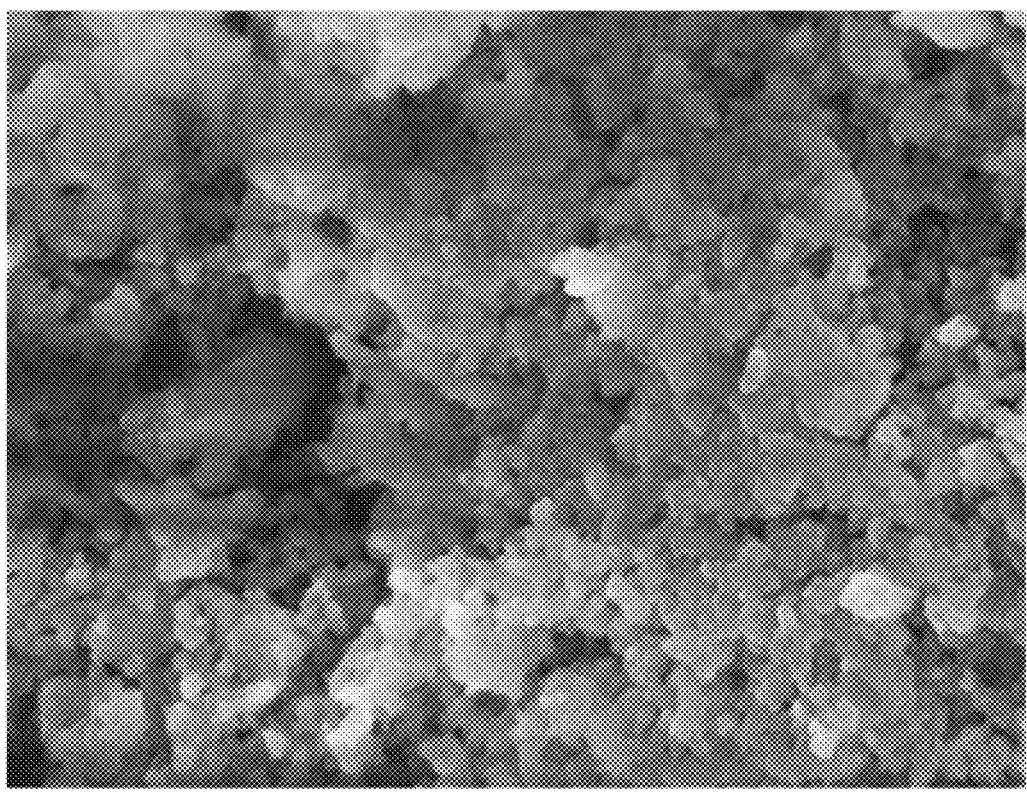
FIG. 2 is an electron microscopic image showing a structure of hyaluronic acid concentrated binder.
Figure 3:
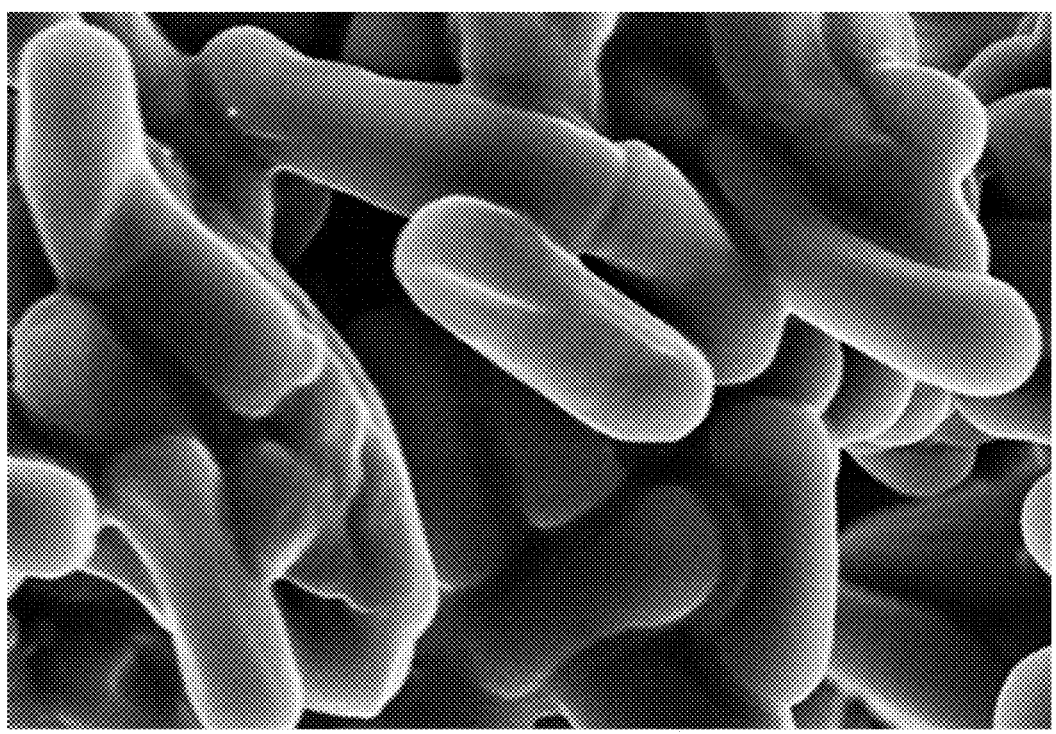
FIG. 3 is an electron microscopic image showing a structure of *Lactobacillus rhamnosus* IDCC 3201 prior to being heat-killed.
Figure 4:
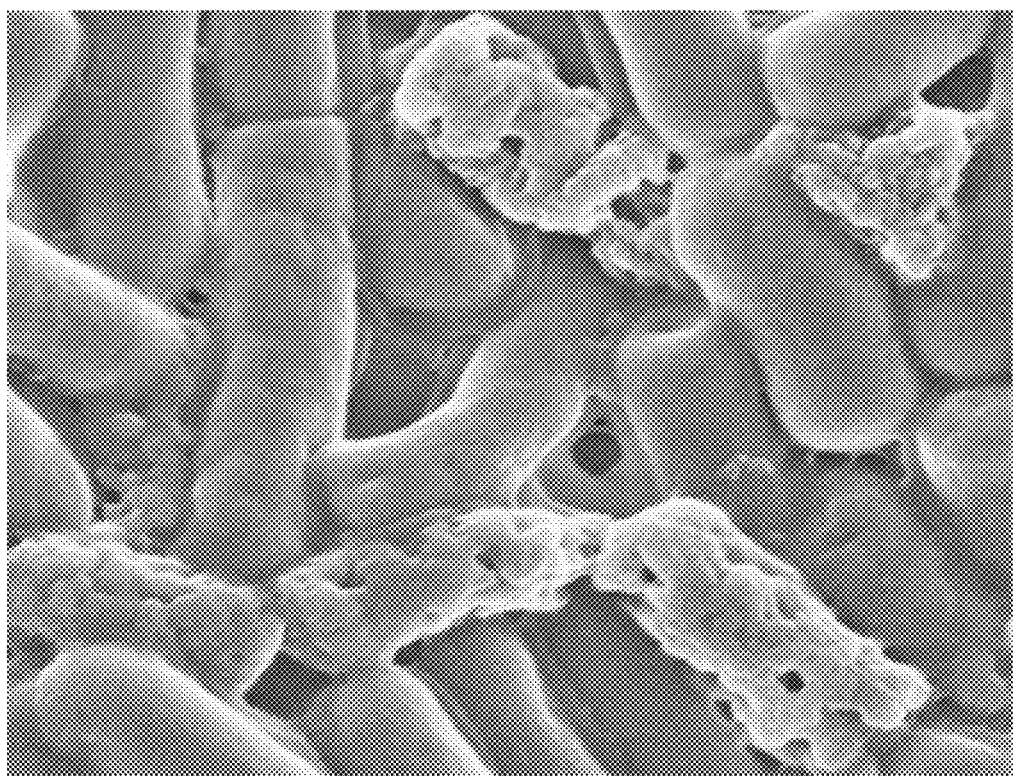
FIG. 4 is an electron microscopic image showing a structure of *Lactobacillus rhamnosus* IDCC 3201 after being heat-killed.
Figure 5:
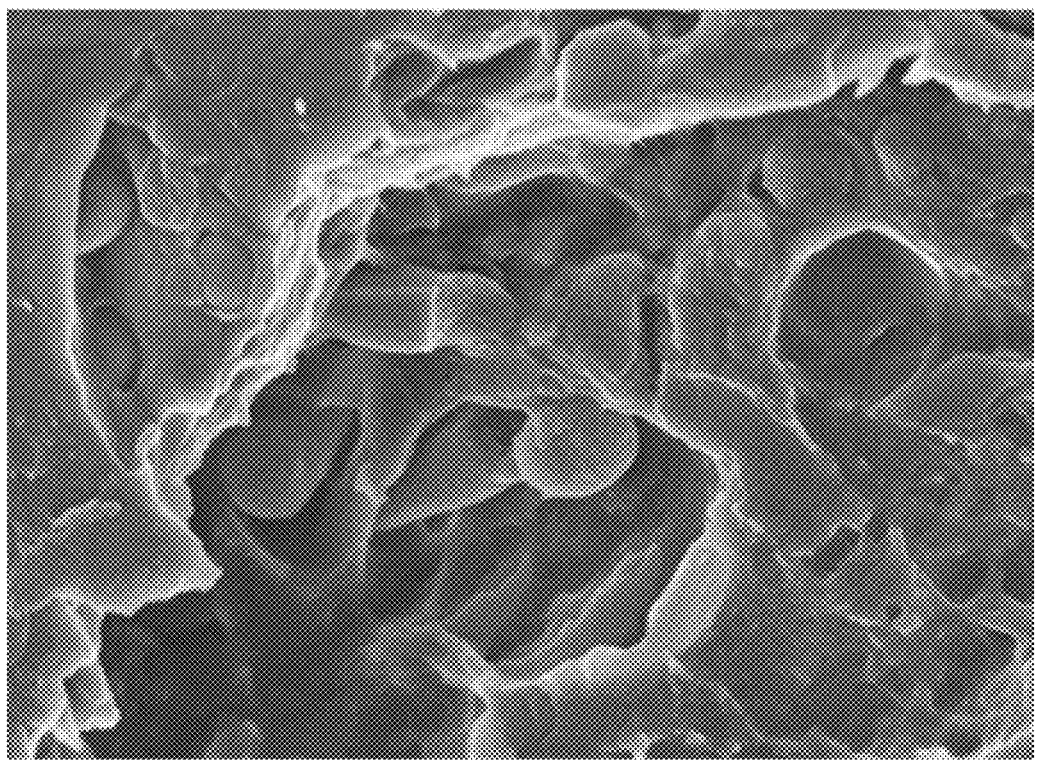
FIG. 5 is an electron microscopic image showing a structure of RHT-3201.

As shown in FIGS. 1 and 2, it was observed that, during the binder preparation process, the *Lactobacillus rhamnosus* IDCC 3201 culture filtrate was mixed with hyaluronic acid, followed by concentration, so hyaluronic acid particles became denser to form a structure of a binder (see FIG. 2). As shown in FIGS. 3 and 4, it was observed that the cellular walls of lactic acid bacteria were not fragmented by heat-killing of bacteria in specific conditions, but has an exposed structure capable of easily adhering to the intestinal mucosa (see FIG. 4). Last, the heat-killed bacteria were mixed with the hyaluronic acid binder to facilitate the adhesion to the intestinal mucosa (see FIG. 5).

Example 6

Mass Production of RHT-3201

In order to investigate reproducibility when RHT-3201 was mass-produced by the preparation method in Example 4 above, the intestinal adhesion rate was compared between a probiotic and mass-produced RHT-3201 (see Table 5).

Specifically, *Lactobacillus rhamnosus* IDCC 3201 was cultured at 37° C. overnight in a fermentation tank with a production scale of 1 ton. The culture filtrate and the bacteria were separated through centrifugation, and hyaluronic acid having 0.001% (w/v) of the volume of the culture liquid was added to the culture filtrate, followed by concentration under reduced pressure at 50° C., thereby preparing a binder, which is to be conjugated to the surface of the heat-killed bacteria. The bacteria were subjected to a heat treatment at 80° C. for 60 minutes, thereby preparing heat-killed bacteria. In addition, the binder and the heat-killed bacteria were mixed, homogenized, and dried, thereby preparing RHT-3201. The *Lactobacillus rhamnosus* IDCC 3201 probiotic used as a control was prepared according to an ordinary process for preparing probiotic raw materials. Specifically, the bacteria were obtained from the same culture liquid, suspended in 20 ml of a phosphate buffer solution, and freeze-dried, thereby preparing a bacterial powder.

TABLE 5

Comparison of adhesion rates bewteen conventional probiotic preparation and RHT-3201 according to the present invention

|  | RHT-3201 | Probiotic preparation |
|---|---|---|
| Adhesion rate (%) | 85 | 54 |

As shown in Table 5, it was verified that the adhesion rate of RHT-3201 showed a 57% improvement compared with the *Lactobacillus rhamnosus* probiotic preparation.

Example 7

Evaluation on Intake Stability

<7-1> Acid Stability

A lactic acid bacteria preparation is exposed to gastric acids when passing through the stomach of the digestive tract. While this environment was reproduced in vitro conditions, the comparison of acid stability between the probiotic bacterium and RHT-3201 of the present invention was conducted. More specifically, 10% HCl was dropped into MRS medium to adjust pH to 2.3 and 2.5, and then the MRS was sterilized for use. 1 g of the probiotic and RHT-3201 samples were respectively put into the pH-adjusted MRS medium, followed by reaction for 0, 1, and 2 hours. The adhesion rate was analyzed by measuring the adhering bacterial count to Caco-2 cells by the same method as in Example <3-2>. Here, the lactic acid bacterium used in the test was *Lactobacillus rhamnosus* IDCC 3201. RHT-3201 prepared by the preparing process in Example 6 and the probiotic were used for the test.

TABLE 6

Acid stability measurement results of RHT-3201 according to the present invention

| Test sample | pH 2.3 ($\times 10^8$ CFU/ml) | | | Ahesion rate (%) | pH 2.5 ($\times 10^8$ CFU/ml) | | | Adhesion rate (%) |
|---|---|---|---|---|---|---|---|---|
|  | 0 | 1 h | 2 h |  | 0 | 1 h | 2 h |  |
| Probiotic bacterium | 1 | 0.1 | 0.04 | 4 | 1 | 0.19 | 0.07 | 7 |
| RHT-3201 | 1 | 0.7 | 0.34 | 34 | 1 | 0.83 | 0.48 | 48 |

As shown in Table 6, it was verified that, compared with the probiotic bacterium, the adhesion efficiency of RHT-3201 of the present invention maintained stable even when exposed to an acid for 2 hours.

<7-2> Bile Stability

The enterohepatic circulation of bile acids is attained such that the bile acids are produced from the liver, leak through the biliary tract, flow into the small intestine, are then 95% absorbed into the ileum, which is the end section of the small intestine, and again enter the liver. The bile acids affect the adhesive ability of lactic acid bacteria settled in the small intestine. Therefore, the difference in the adhesion rate between the probiotic bacterium and RHT-3201 of the present invention when exposed to bile acids was compared. More specifically, the MRS media with and without 0.3% bile acids added thereto was used after being sterilized. Then, 1 g of the probiotic bacterium and RHT-3201 of the present invention were inoculated in the media, respectively, followed by reaction for 2 hours. Subsequently, the adhesion rate was analyzed by measuring the adhering bacterial count to Caco-2 cells by the same method as in Example <3-2>.

Here, the lactic acid bacterium used in the test was *Lactobacillus rhamnosus* IDCC 3201. RHT-3201 prepared by the preparing process in Example 6 and the probiotic were used for the test.

TABLE 7

Bile stability results of RHT-3201 according to the present invention

| Test sample | MRS ($\times 10^8$ CFU/ml) | MRS + 0.3% bile ($\times 10^8$ CFU/ml) | Adhesion rate (%) |
|---|---|---|---|
| Probiotic bacterium | 1 | 0.23 | 23 |
| RHT-3201 | 1 | 0.57 | 57 |

As shown in Table 7, it was verified that, when exposed to bile acids for 2 hours, the adhesion efficiency of RHT-3201 maintained at 57%, which was about 2.5-fold higher than that of the probiotic bacterium.

Example 8

Evaluation on Stability Over Time by Temperature

<8-1> Comparative Test of Stability Over Time at 4° C. Between RHT-3201 and a Probiotic Bacterium RHT-3201 of the present invention prepared in Example 6 above and a probiotic bacterium were stored in a refrigerator at 4° C. for 365 days, and then the adhering bacterial count per 1 g of a raw material was measured over time. The results are shown in Table 8. The adhering bacterial count was measured by the same method as in Example <3-2>. The adhesion rate was analyzed by measuring the adhering bacterial count to Caco-2 cells.

TABLE 8

Comparative test of stability over time at 4° C. between RHT-3201 according to the present invention and a probiotic bacterium

| Test sample | Stability over time at 4° C. | | | | Residual adhesion rate (%) |
|---|---|---|---|---|---|
| | 0 day | 60 days | 180 days | 365 days | |
| Probiotic bacterium | 65% | 52% | 34% | 19% | 29.2 |
| RHT-3201 | 82% | 71% | 52% | 45% | 54.8 |

<8-2> Comparative Test of Stability with Time at 15° C. Between RHT-3201 and Probiotic RHT-3201 of the present invention prepared in Example 6 above and a probiotic were stored in a refrigerator at 15° C. for 365 days, and then the adhering bacterial count per 1 g of a raw material was measured over time. The results are shown in Table 9. The adhering bacterial count was measured by the same method as in Example <3-2>. The adhesion rate was analyzed by measuring the adhering bacterial count to Caco-2 cells.

TABLE 9

Comparative test of stability over time at 15° C. between RHT-3201 according to the present inventio and a probiotic bacterium

| Test sample | Stability over time at 15° C. | | | | Residual ahesion rate (%) |
|---|---|---|---|---|---|
| | 0 day | 60 days | 180 days | 365 days | |
| Probiotic bacterium | 65% | 46% | 29% | 15% | 23.1 |
| RHT-3201 | 82% | 66% | 59% | 38% | 46.3 |

<8-3> Comparative Test of Stability Over Time at 25° C. Between RHT-3201 and a Probiotic Bacterium RHT-3201 of the present invention prepared in Example 6 above and a probiotic bacterium were stored in a refrigerator at 25° C. for 365 days, and then the adhering bacterial count per 1 g of a raw material was measured over time. The results are shown in Table 10. The adhering bacterial count was measured by the same method as in Example <3-2>. The adhesion rate was analyzed by measuring the adhering bacterial count to Caco-2 cells.

TABLE 10

Comparative test of stability over time at 25° C. between RHT-3201 according to the present invention and a probiotic bacterium

| Test sample | Stability with time at 25° C. | | | | Residual adhesion rate (%) |
|---|---|---|---|---|---|
| | 0 day | 60 days | 180 days | 365 days | |
| Probiotic bacterium | 65% | 39% | 25% | 12% | 18.4 |
| RHT-3201 | 82% | 56% | 49% | 35% | 42.6 |

<8-4> Comparative Test of Stability Over Time at 37° C. Between RHT-3201 and a Probiotic Bacterium RHT-3201 of the present invention prepared in Example 6 above and a probiotic were stored in a refrigerator at 37° C. for 365 days, and then the adhering bacterial count per 1 g of a raw material was measured over time. The results are shown in Table 11. The adhering bacterial count was measured by the same method as in Example <3-2>. The adhesion rate was analyzed by measuring the adhering bacterial count to Caco-2 cells.

TABLE 11

Comparative test of stability over time at 37° C. between RHT-3201 according to the present invention and a probiotic bacterium

| Test sample | Stability over time at 37° C. | | | | Residual adheson rate (%) |
|---|---|---|---|---|---|
| | 0 day | 60 days | 180 days | 365 days | |
| Probiotic bacterium | 65% | 29% | 15% | 8% | 12.3 |
| RHT-3201 | 82% | 46% | 44% | 32% | 39.0 |

Example 9

Regulation of Cytokine Production by RHT-3201 in Mild Atopic Dermatitis-Induced In Vitro Models In mild atopic dermatitis-induced mouse models, the effects of RHT-3201 according to the present invention, a probiotic, and a killed bacterial preparation, which were produced from the same lactic acid bacteria, were evaluated, while the specific test method was as follows.

<9-1> Preparation of Samples

RHT-3201 of the present invention and a probiotic preparation were prepared by the same method as in Example 6 above, using a culture liquid prepared by culturing *Lactobacillus rhamnosus* IDCC 3201 in MRS medium containing 0.1-1% whey powder at 37° C. for 24 hours.

For killed bacteria, bacteria was obtained from the culture liquid, suspended in 500 µl of a phosphate buffer solution, and dried through freeze-drying. The dried bacteria was weighed, and suspended in a sterile phosphate buffer to reach 300 mg/ml. The suspension was heat-treated at 100° C. for 30 minutes, so the bacteria were killed. The three types of samples were diluted with a phosphate buffer solution to prepare 1 µg/ml of final samples, respectively. Skimmed milk powder was used as a control.

<9-2> Culture of Spleen Cells and Measurement of Cytokines

Spleen cells were prepared by the same method as in Example <1-2>. 200 µl of spleen cell suspension ($5 \times 10^6$ cells/ml) and 10 µl (1 µg/ml) of each sample liquid prepared in Example <9-1> were added to each well of a 96-well plate, followed by culturing in a 5% $CO_2$ incubator for 7 days. After the completion of the culture, IL-4 and IL-12 levels in the culture liquid were measured using the Cytoset kit (Biosource). The levels of IL-4 and IL-12 production by each sample were expressed as a rate of increase thereof compared with the control as shown in Table 12.

TABLE 12

Increase rate of cytokines from spleen cells upon the addition of lactic acid bacteria sample

| Sample | Increase (%) compared with control | | IL-4/IL-12 ratio |
|---|---|---|---|
| | IL-4 | IL-12 | |
| *Lactobacillus rhamnosus* IDCC 3201 (probiotic bacterium) | 20 | 29 | 0.68 |
| *Lactobacillus rhamnosus* IDCC 3201 (killed bacterium) | 12 | 34 | 0.35 |
| RHT-3201 | 3 | 67 | 0.04 |

As test results, a 20% increase in IL-4 production and a 29% increase in IL-12 production were shown in the *Lactobacillus rhamnosus* IDCC 3201 probiotic bacterium. A 12% increase in IL-4 production and a 34% increase in IL-12 production were shown in the killed bacteria. A 3% increase in IL-4 production and a 67% increase in IL-12 production were shown in RHT-3201. Therefore, it was verified that RHT-3201 of the present invention, which showed a significant increase in IL-12 production and a relatively mild increase in IL-4 production, had the most excellent effect in the regulation of cytokine production.

Example 10

Therapeutic Effect of RHT-3201 According to the Present Invention in Severe Atopic Dermatitis-Induced In Vivo Models <10-1> Preparation of Test Material and Inducible Antigen RHT-3201 according to the present invention was used as a test material, while steroid-based dexamethasone (Sigma Co. Ltd), which is used as a main therapeutic agent for severe atopic dermatitis, was used as a positive control. An extract of Dermatophagoides farina, which is a major species of house dust mite, was used as an atopy inducing material. The extract was purchased in an ointment form from Central Lab. Animal Inc.

The dexamethasone was prepared by being dissolved in ethanol into a concentration of 0.1% (w/v), and RHT-3201 of the present invention was prepared by being dissolved in distilled water to doses of $1\times10^8$ CFU/0.5 ml/mouse, $1\times10^9$ CFU/0.5 ml/mouse, and $1\times10^{10}$ CFU/0.5 ml/mouse, respectively. All the samples to be administered were prepared on the testing day. The dexamethasone was coated on the skin of a testing subject at 100 μl for each subject twice a week, while RHT-3201 according to the present invention was orally administered at 0.5 ml for each subject using a mouse zonde once a day. Distilled water was administered for a normal group and an atopy control group. The administration was conducted for 8 weeks in all the test groups.

<10-2> Preparation and Breeding of Test Animals

Female NC/Nga mice (6-week aged) were purchased from Central Lab. Animal Inc., and acclimated for 1 week before use. The breeding environment was as follows: constant temperature (22±2° C.) and constant humidity (50-60%) were maintained, while cycles of light (08:00~20:00) and dark (20:00~08:00) were controlled at an interval of 12 hours. Three animals were allocated and bred in each polysulfone cage, being fed with free access to a test diet and water for 24 hours.

<10-3> Induction of Severe Atopic Dermatitis

The dosal areas up to the upper portions of auricles of the NC/Nga 7-week aged mice were completely shaved, and 150 μl of an aqueous solution of 4% sodium dodecyl sulfate (SDS) was then sprayed on the shaved parts. After complete drying, 100 mg of an ointment for dust mites (mite extract) was uniformly coated on the shave parts. The ointment for dust mites (mite extract) was coated twice a week for three weeks, a total of six times, to induce moderate or more severe dermatitis. Thereafter, the ointment was coated once a week during an administration period to the test groups (8 weeks), thereby maintaining severe atopic dermatitis.

TABLE 13

Sever atopic dermatitis inductin scores in each model before treatement with test materials

| | Severe atopic dermatitis score Mean ± SE (n = 6) |
|---|---|
| Normal group | 0 |
| Atopy control (Vehicle) | 11.0 ± 0.4 |
| Dexamethasone (Postive control) | 10.8 ± 0.4 |
| RHT-3201    1 × 10⁸ CFU/mouse | 10.8 ± 0.4 |
|             1 × 10⁹ CFU/mouse | 10.7 ± 0.3 |
|             1 × 10¹⁰ CFU/mouse | 10.7 ± 0.3 |

As shown in Table 13, as a result of inducing severe atopic dermatitis by coating the ointment for dust mites (mite extract) on the NC/Nga mice for three weeks, the mean score for each group was 10 or higher, so the NC/Nga mice with severe atopic dermatitis were prepared.

<10-4> Evaluation of Atopic Dermatitis

In the present evaluation, the severity of atopic dermatitis was expressed as a total of evaluation scores of five items, using SCORAD (SCORing Atopic Dermatitis), which is a generally used method for clinical macroscopic evaluation. The items were erythema, dry skin, edema, excoriation, and lichenification. The scores for the five items (no symptom (score 0), mild symptom (score 1), moderate symptom (score 2), severe symptom (score 3) for each item) were added up, while the evaluation score was determined between the lowest score of 0 (a state in which there is no symptom) and the highest score of 15 (a state in which the symptoms for all items were severe). The severity of the mouse skin lesions was evaluated every week (see FIG. 6).

Figure 6:
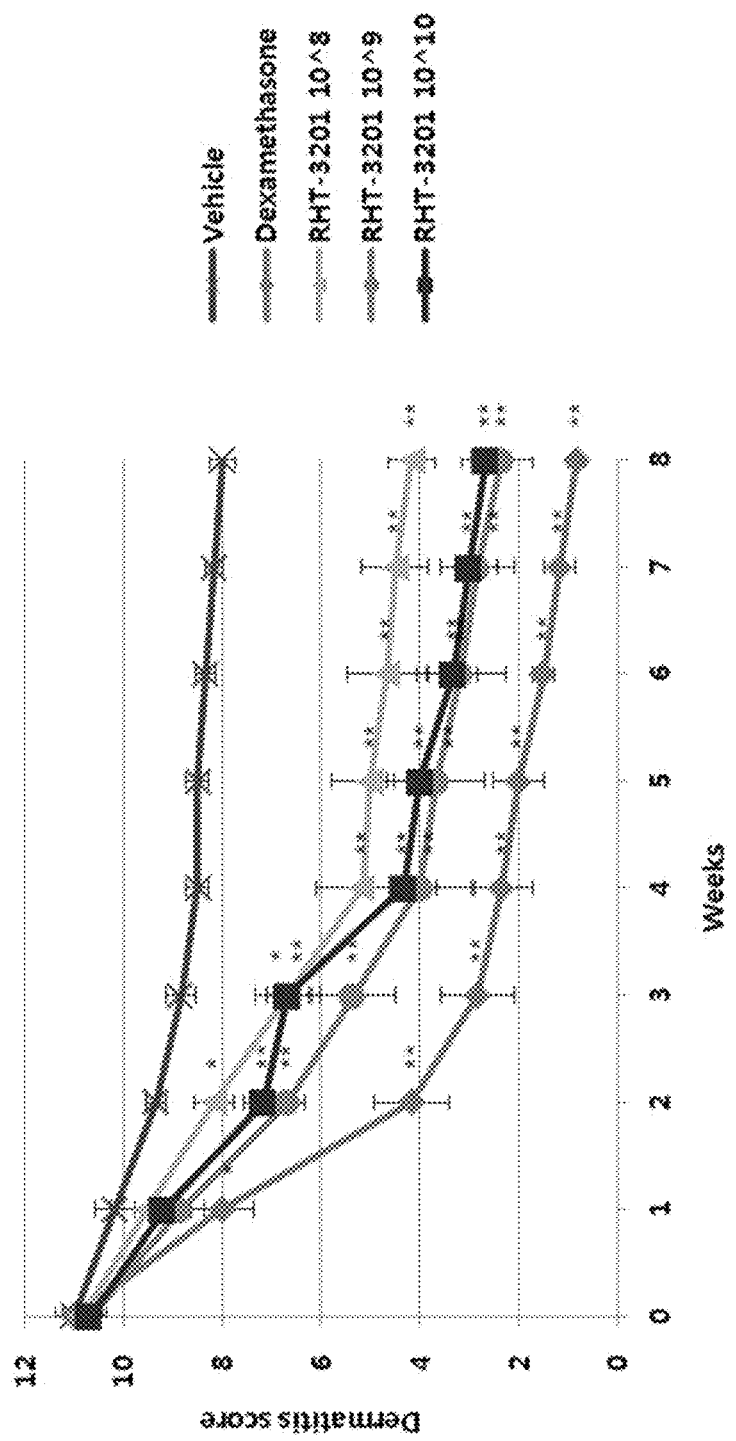
FIG. 6 illustrates SCORAD index evaluation scores of the therapeutic effect of RHT-3201 according to the present invention in severe atopic dermatitis models.

In FIG. 6, vehicle represents the results for the mouse group having dust mite-inducing severe atopic dermatitis, and dexamethasone represents the results for the mice group skin-coated with medication using dexamethasone as a positive control for 8 weeks. RHT-3201 10^8, RHT-3201 10^9, and RHT-3201 10^10 represent the results for the mouse groups having dust mite-inducing severe atopic dermatitis administered with RHT-3201 of the present invention at different concentrations: RHT-3201 10^8 represents the results for the treatment mouse group orally administered at $1\times10^8$ CFU/mouse for 8 weeks; RHT-3201 10^9 represents the results for the treatment mouse group orally administered at $1\times10^9$ CFU/mouse for 8 weeks; and RHT-3201 10^10 represents the results for the treatment mouse group orally administered at $1\times10^{10}$ CFU/mouse for 8 weeks.

As a result of investigating the effect of alleviating the severe atopic dermatitis after 8-week treatment, it was verified from the results in FIG. 6 that the severe atopic dermatitis score in the vehicle group without any medicinal treatment was, as a mean value, 8.0, indicating that the initial severity state was maintained. When compared with the mouse group having dust mite-inducing severe atopic dermatitis (vehicle group), the evaluation of the severity of the mouse skin lesions was significantly deceased in all the groups treated with RHT-3201 10^8, RHT-3201 10^9, and RHT-3201 10^10, respectively. More specifically, the RHT-3201 10^8 administration group showed a severe atopic dermatitis score of 4.2, resulting in a severe atopic dermatitis alleviation efficiency of 47.5%. The RHT-3201 10^9 administration group showed a severe atopic dermatitis score of 2.3, resulting in a severe atopic dermatitis alleviation efficiency of 71.25%. The RHT-3201 10^10 administration group showed a severe atopic dermatitis score of 2.7, resulting in a severe atopic dermatitis alleviation efficiency of 66.25%.

It has been generally known that lactic acid bacteria preparations need to be taken in large quantities without any report about optimal concentrations of such preparations for obtaining the effect of alleviating the severe atopic dermatitis. The reason is that, as for lactic acid probiotics, the lactic acid bacteria are killed in large quantities by gastric and bile acids while passing through the gastrointestinal tract, causing the reduction in adhesion efficiency to the intestinal mucosa capable of exhibiting immune actions, and thus are excreted from the body. Unlike this, RHT-3201 of the present invention was shown to definitely possess a therapeutic effect at its different concentrations. The $\times 10^9$ and $\times 10^{10}$ intake units showed similarity within an error range regarding the efficacy of alleviating the severe atopic dermatitis. The reason is that the combination number with the toll-like receptor distributed in dendritic cells of the intestinal mucosa is saturated to have a threshold.

Figure 7:
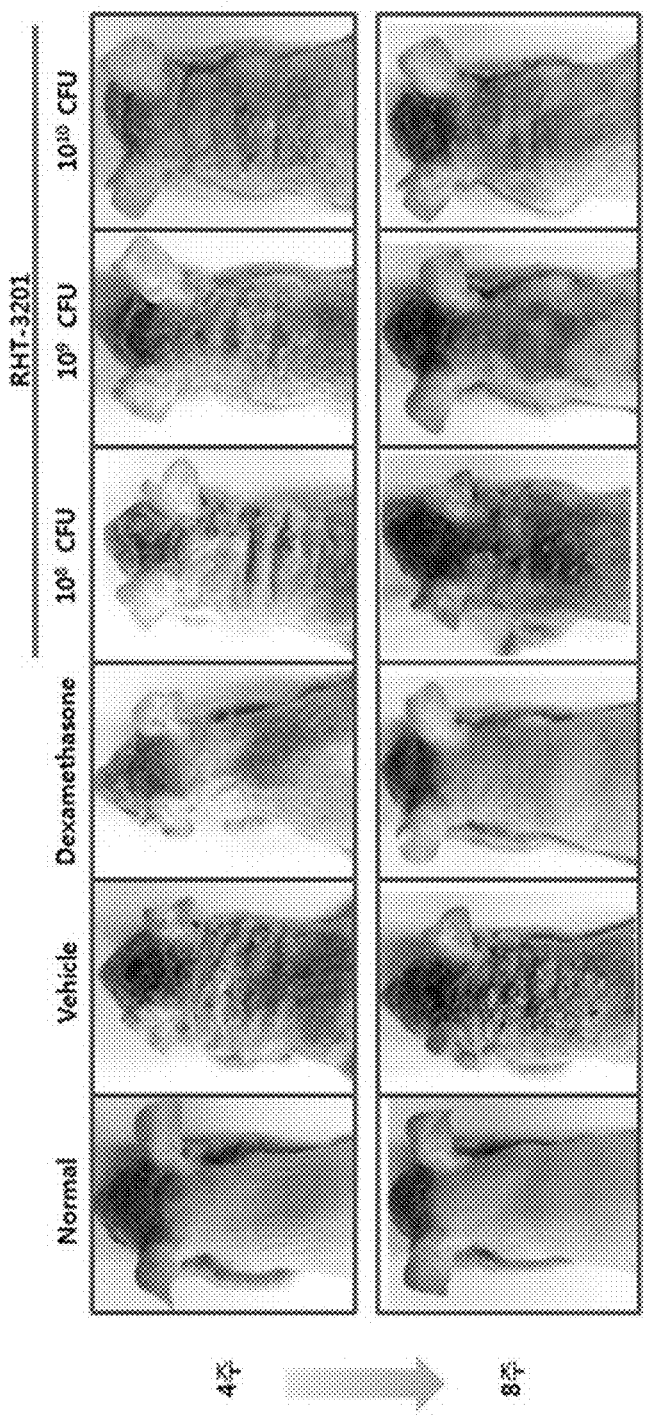
FIG. 7 illustrates macroscopic observation results of the treatment effect of RHT-3201 according to the present invention in severe atopic dermatitis models.

FIG. 7 illustrates macroscopic observation results of the therapeutic effect of *Lactobacillus* RHT-3201 on severe atopic dermatitis upon its oral administration. In the skin lesions of the vehicle group, dry skin, erythema, edema, lichenification, and scratches due to pruritus-induced continuous scratching were distinctly observed. It was macroscopically investigated that the atopic dermatitis severity was improved in the RHT-3201 administration groups of all the concentrations.

<10-5> Scratching Behavior and Body Weight Measurement

The number of scratching behaviors for 15 minutes was counted once a week from week 1 of administration of a test drug. Only the number of scratching behaviors using a hind leg was counted in order to avoid counting scratching behaviors due to the other causes besides scratching behaviors due to pruritus. Meanwhile, the weight loss tends to occur due to side effects of drugs and stress at the time of inducing severe atopic dermatitis. In order to investigate whether the side effect of weight loss occurs by the test materials of the present invention, the test animals were weighed during the administration period of the test materials.

Figure 8:
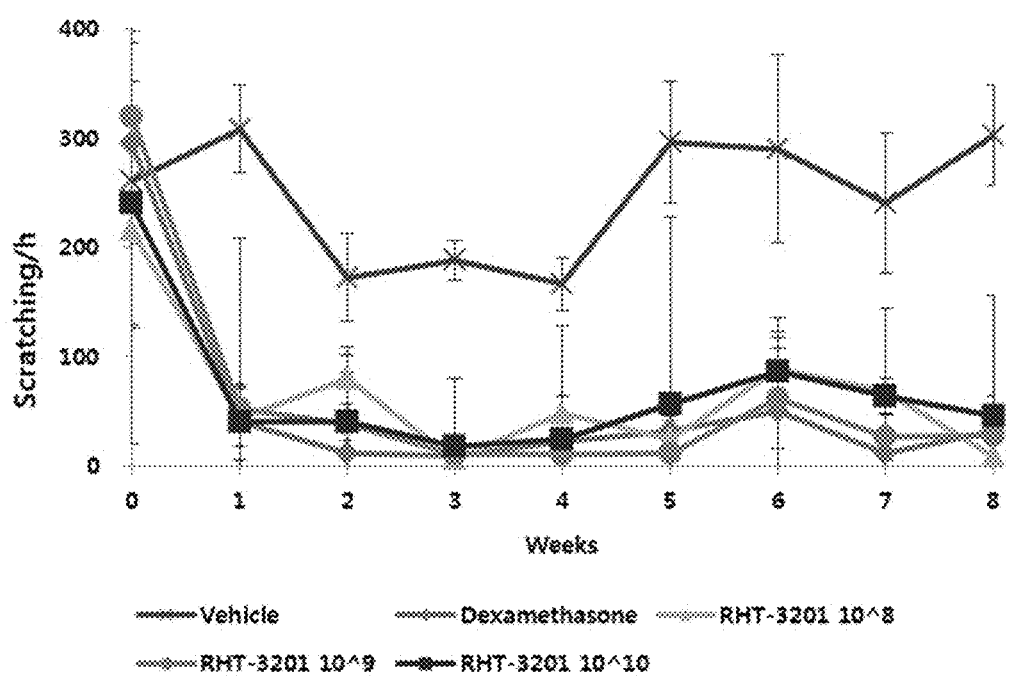
FIG. 8 illustrates the change in scratching behavior according to the administration of RHT-3201 of the present invention.

As shown in FIG. 8, the number of scratching behaviors was measured to be 100/hr or less in all the test material administration groups during eight weeks, while the number of scratching behaviors showed a decrease tendency every week, compared with the vehicle group. On weeks 3, 6, and 8, there was significances in the groups administered with RHT-3201 with all concentrations compared with the vehicle group.

Figure 9:
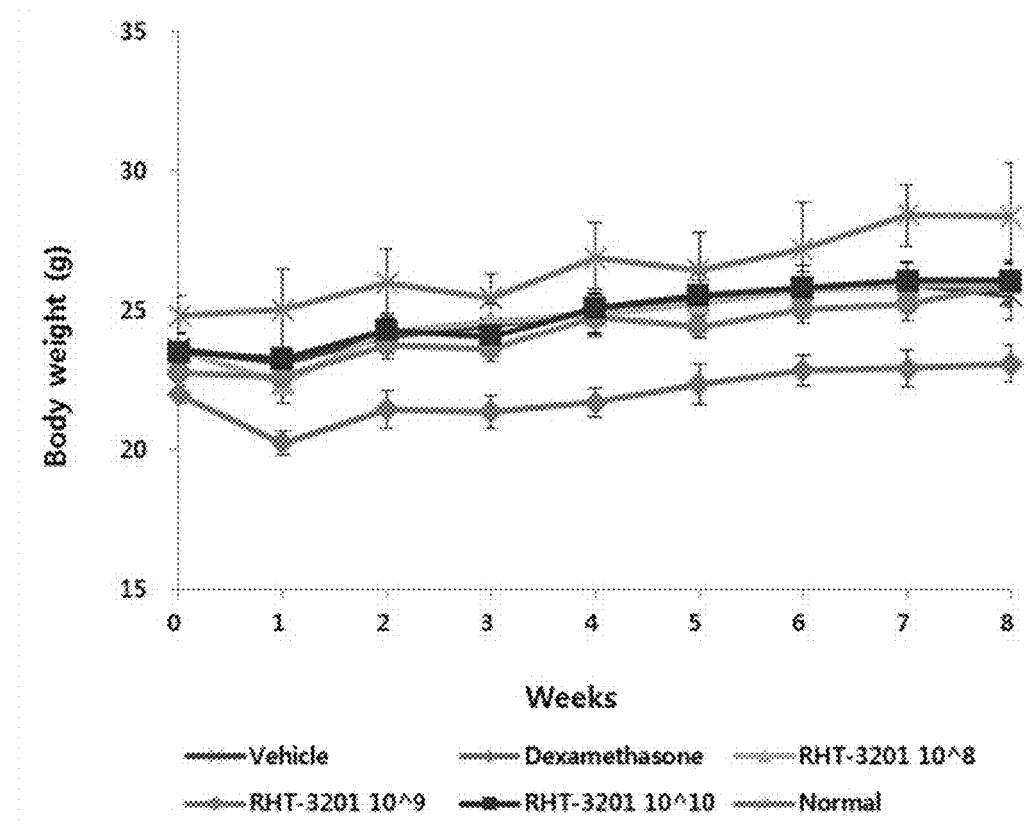
FIG. 9 illustrates the change in body weight according to the administration of RHT-3201 of the present invention.

In addition, as shown in FIG. 9, the transdermal administration of dexamethasone as a positive control during eight weeks caused a weight loss for 4 weeks, whereas the administration of RHT-3201 of the present invention showed a weight gain in the same manner as in the normal group, causing no side effect of weight loss, and thus RHT-3201 of the present invention was confirmed to be safe.

<10-6> Measurement of Serum IgE Level

After the administration of test drugs for eight weeks, the blood was taken through the retro-orbital venous plexus, and centrifuged at 12,000 RPM for 10 minutes to separate the serum. The serum IgE level was measured using an ELISA kit (SHIBAYAGI, Japan).

Figure 10:
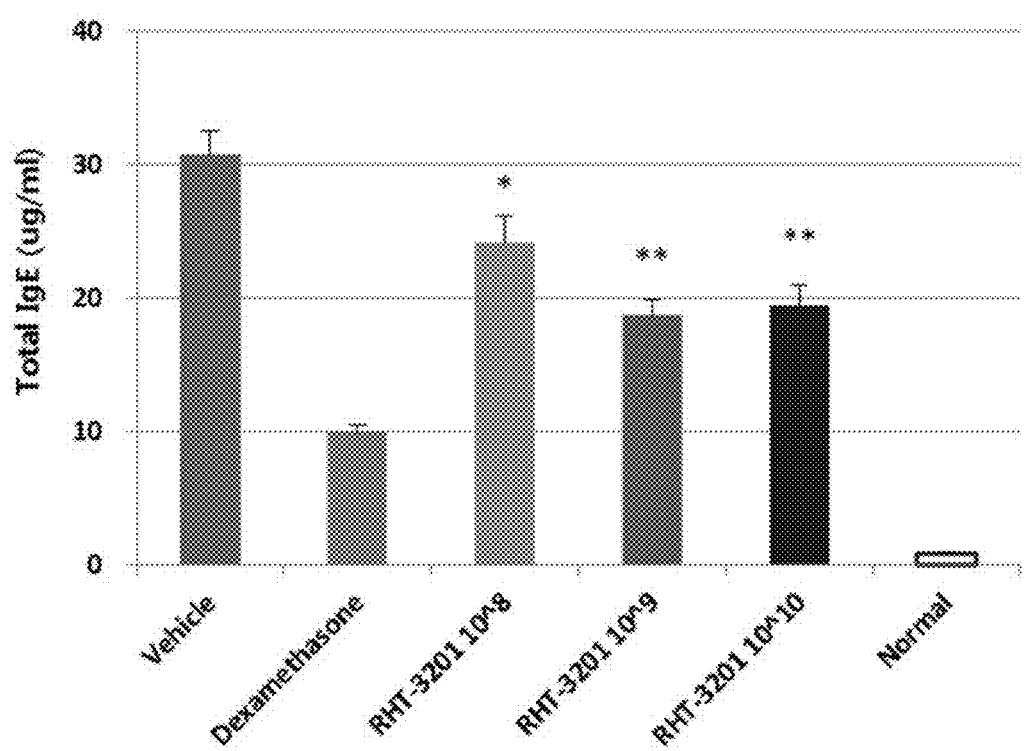
FIG. 10 illustrates the change in blood IgE level according to the administration of RHT-3201 of the present invention.

As shown in FIG. 10, with respect to the IgE that is known to specifically increase at the time of inducing severe atopic dermatitis, the RHT-3201 administration groups according to the present invention showed significant inhibitory effects, while, especially, in the comparative evaluation among different concentrations, the $\times 10^9$ intake unit showed the highest inhibitory effect.

<10-7> Cytokine Producing Ability of Lymph Node Cells

After the end of administration of test materials, each of the severe atopic dermatitis-induced NC/Nga mice was sacrificed. The size and weight of the axillary lymph nodes were measured. In addition, the cell suspensions obtained from the axillary lymph nodes were dispensed in the RPMI-1640 medium (containing 10% FBS, 1% penicillin, and 1% streptomycin) to a concentration of $5 \times 10^6$ cells/ml. The extract of dust mite (*D. farina*) was added to obtain a final concentration of 10 μg/ml, and cultured for 48 hours in a 5% $CO_2$ incubator at 37° C. The supernatant was taken to measure IFN-γ, IL-4, IL-10, and IL-12 production yields using an ELISA kit (IFN-γ & IL-4 manufacturer: R&D SYSTEMS, USA; and IL-10 & IL-12 manufacturer: SIGMA ALDRICH, USA).

Figure 11:
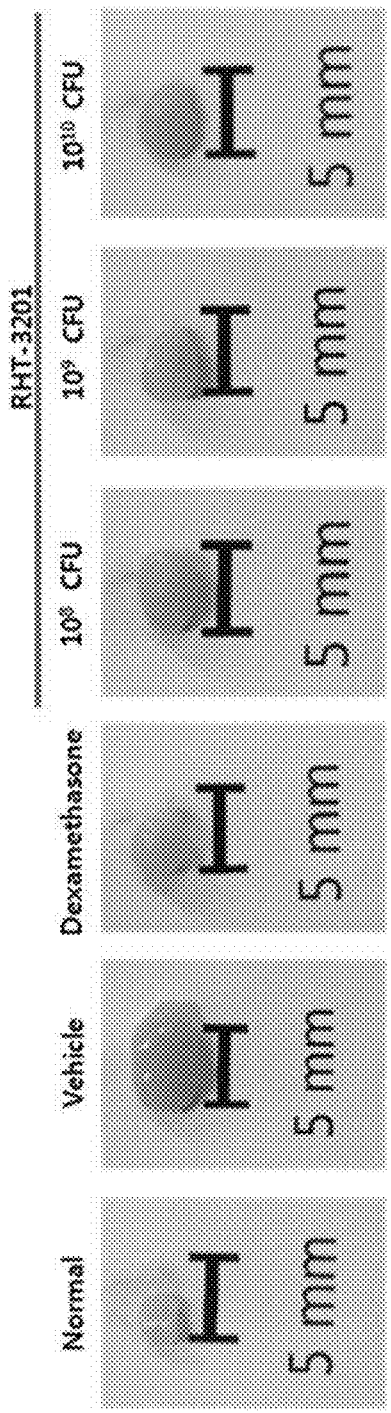
FIG. 11 illustrates macroscopic observation results of the change in mouse lymph nodes according to the administration of RHT-3201 of the present invention in severe atopic dermatitis models.
Figure 12:
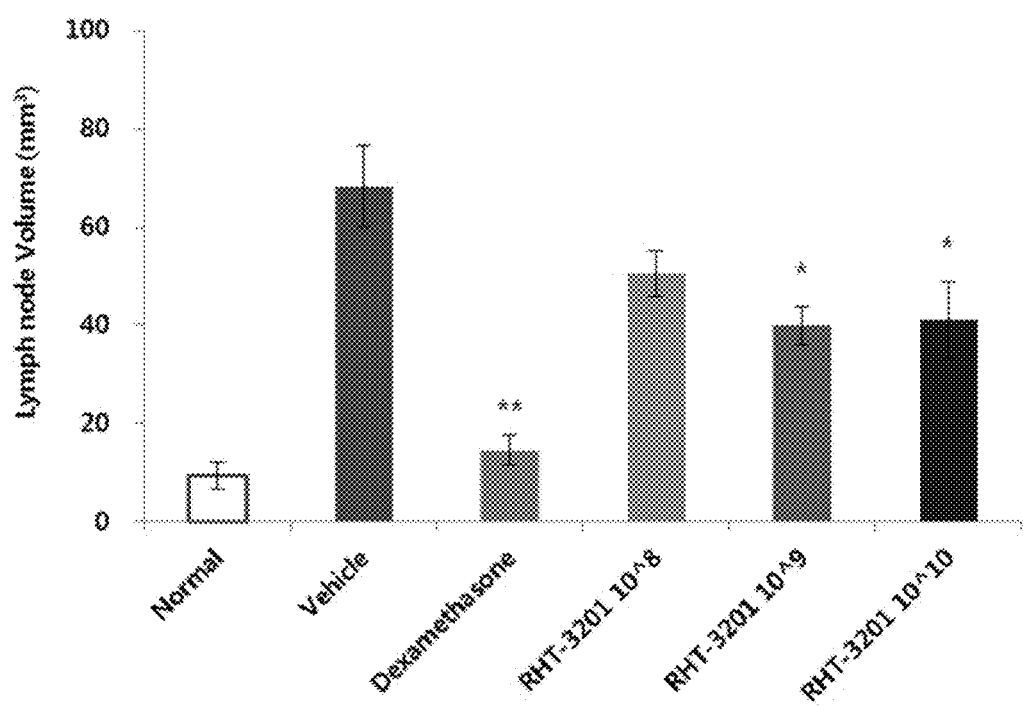
FIG. 12 illustrates the size change of mouse lymph nodes according to the administration of RHT-3201 of the present invention in severe atopic dermatitis models.
Figure 13:
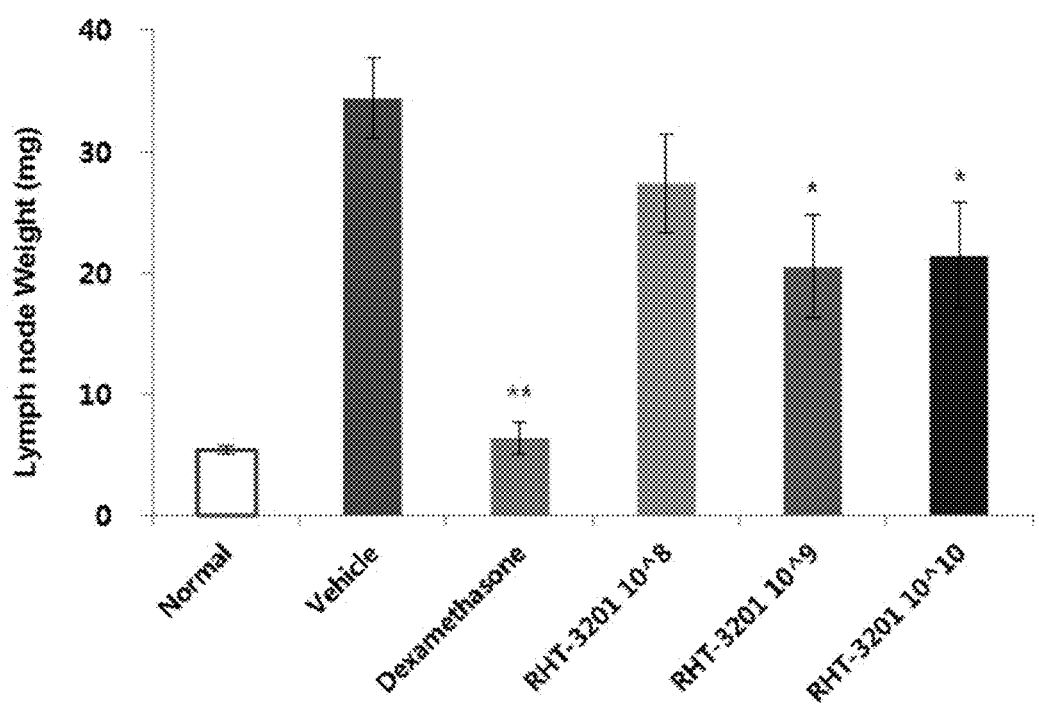
FIG. 13 illustrates the weight change of mouse lymph node according to the administration of RHT-3201 of the present invention in severe atopic dermatitis models.
Figure 14:
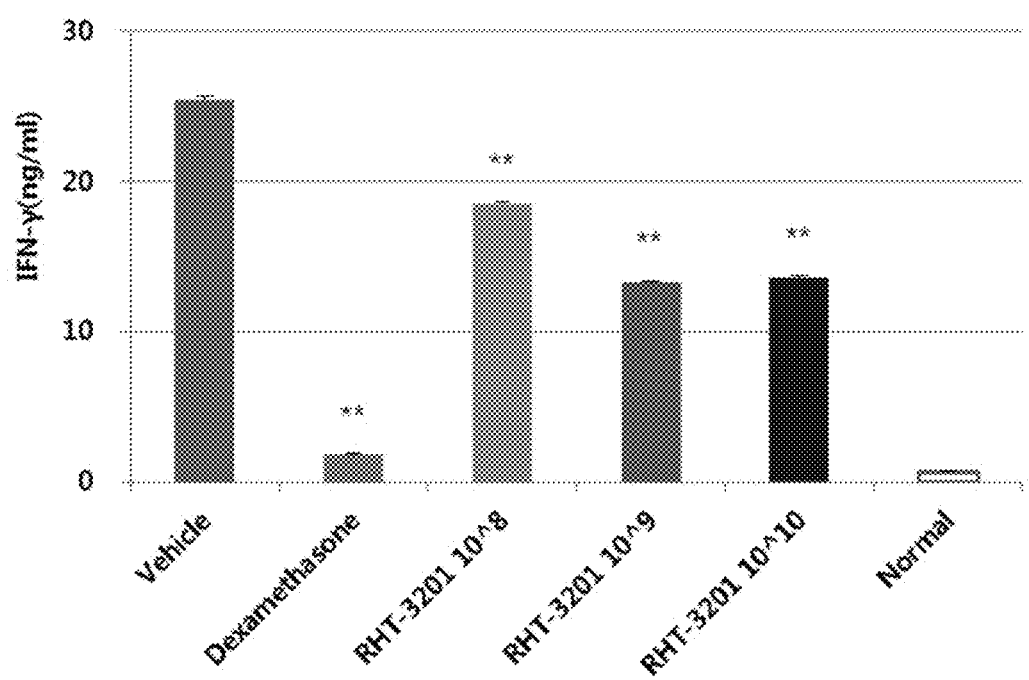
FIG. 14 illustrates the change in IFN-γ production according to the administration of RHT-3201 of the present invention in severe atopic dermatitis models.
Figure 15:
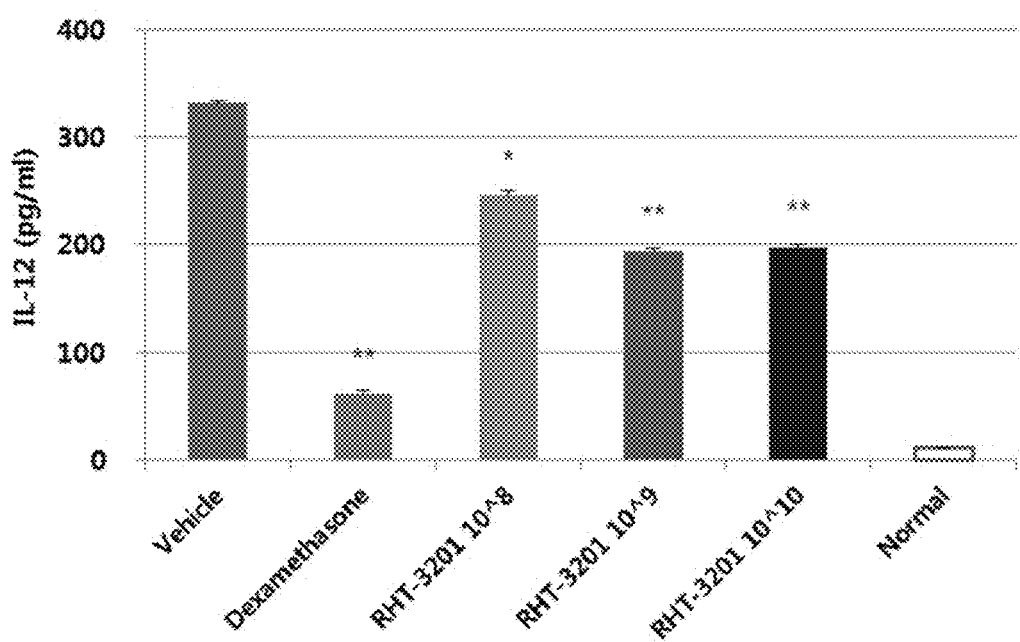
FIG. 15 illustrates the change in IL-12 production according to the administration of RHT-3201 of the present invention in severe atopic dermatitis models.
Figure 16:
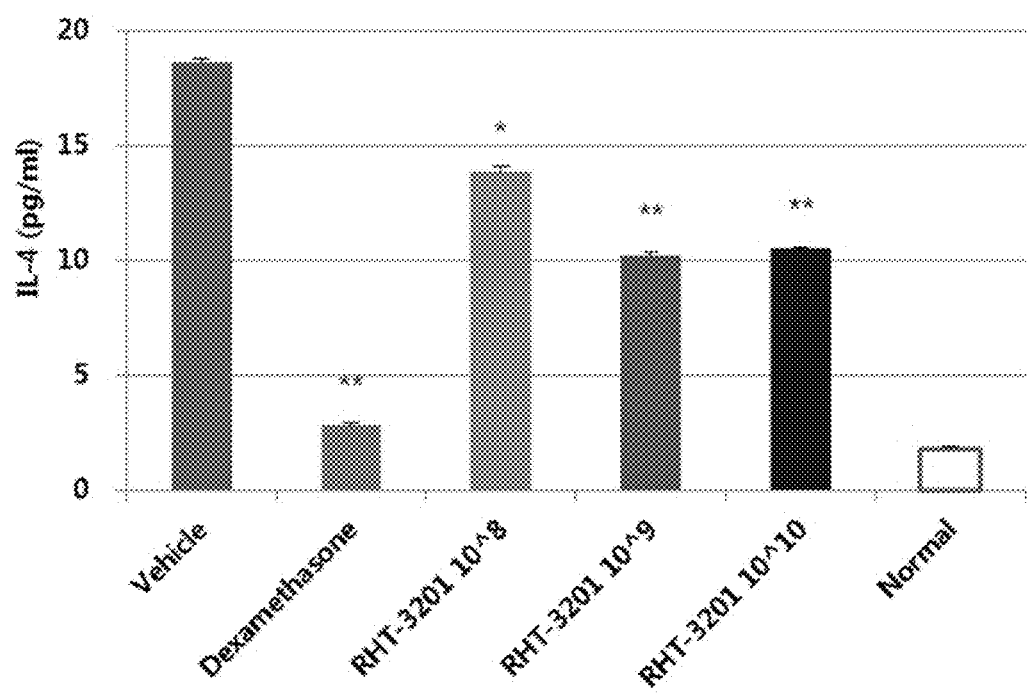
FIG. 16 illustrates the change in IL-4 production according to the administration of RHT-3201 of the present invention in severe atopic dermatitis models.
Figure 17:
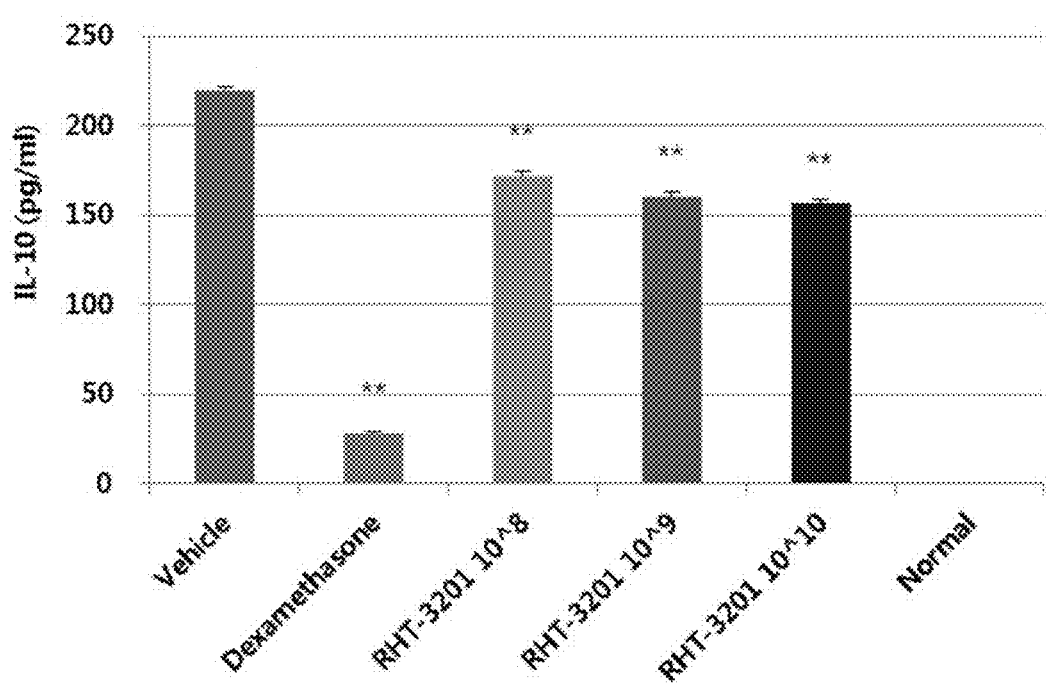
FIG. 17 illustrates the change in IL-10 production according to the administration of RHT-3201 of the present invention in severe atopic dermatitis models.

As shown in FIG. 11, the axillary lymph nodes were involved in the immune response of the dorsal skin of NC/Nga mice, while the lymph nodes of the vehicle group were enlarged due to the exposure to dust mite (mite extract) antigen. As shown in FIGS. 12 and 13, the volume and weight measurement values of the lymph nodes were 70 mm³ and 35 mg, respectively, which were 5-fold and 7-fold higher compared with the normal group. While, the size of the axillary lymph nodes in the severe atopic dermatitis-induced NC/Nga mice was significantly reduced in the RHT-3201 administration groups.

For the confirmation of the cytokine producing ability according to the administration of RHT-3201, the axillary lymph node in the severe atopic dermatitis-induced NC/Nga mice was exposed to the dust mite antigen, and then the levels of cytokines involved in the immune response were measured. The results are shown in FIGS. 14 to 21. It was verified that the administration of RHT-3201 of the present invention significantly reduced Th1-type cytokine IFN-γ (see FIG. 14) and an inducer thereof, IL-12 (see FIG. 15), compared with the vehicle. It was also verified that the administration of RHT-3201 of the present invention significantly reduced Th2-type cytokine IL-4 (see FIG. 16), compared with the vehicle. The main secretory cells of IL-10 in the lymph nodes, i.e., regulatory T cells, perform an immunosuppressive action of inhibiting the Th1 and Th2 reaction. It was also verified that the administration of RHT-3201 significantly reduced IL-10 (see FIG. 17), compared with the vehicle.

Figure 18:
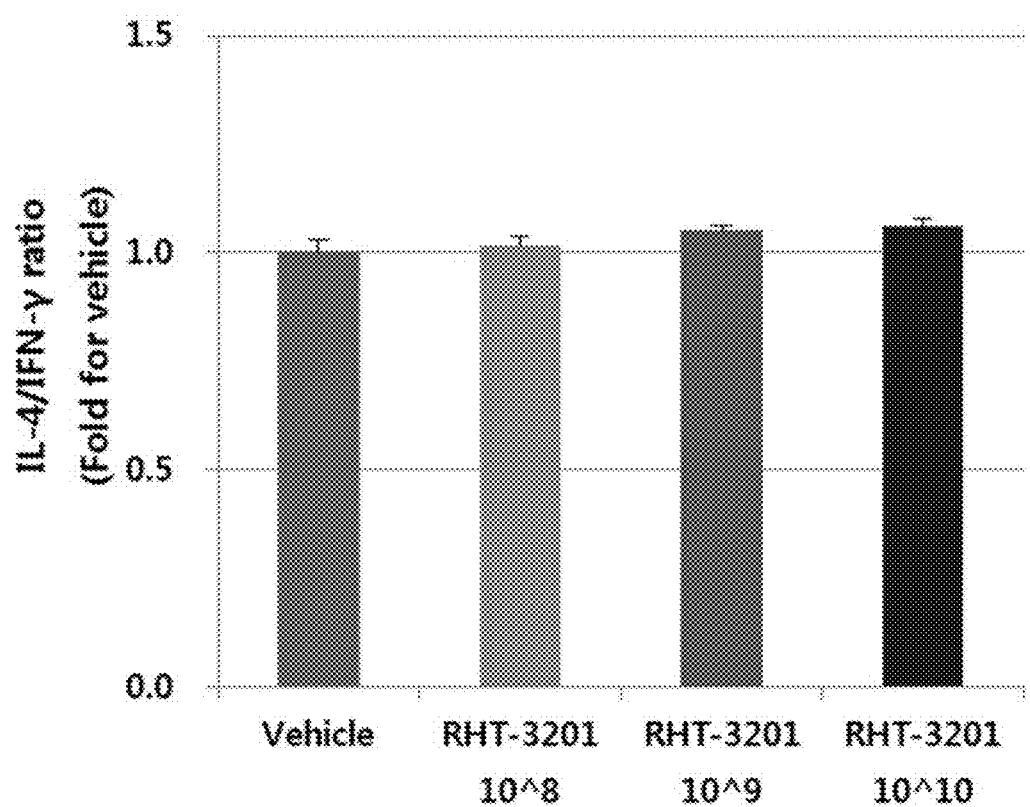
FIG. 18 illustrates the IL-4/IFN-γ ratio according to the administration of RHT-3201 of the present invention in severe atopic dermatitis models.
Figure 19:
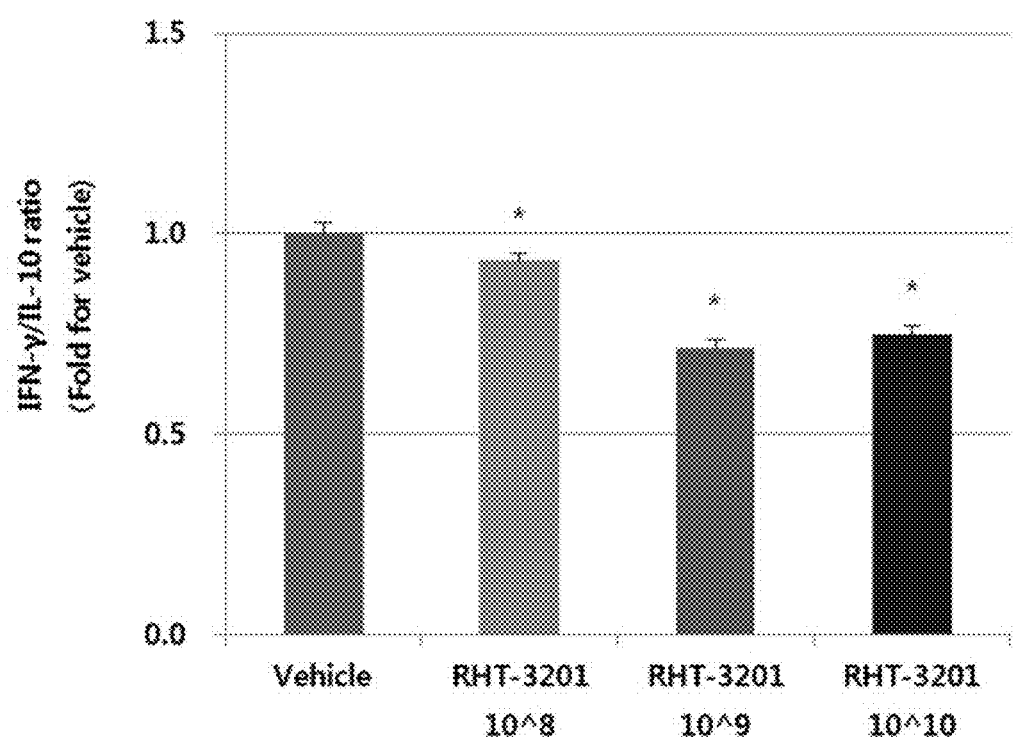
FIG. 19 illustrates the IFN-γ/IL-10 ratio according to the administration of RHT-3201 of the present invention in severe atopic dermatitis models.
Figure 20:
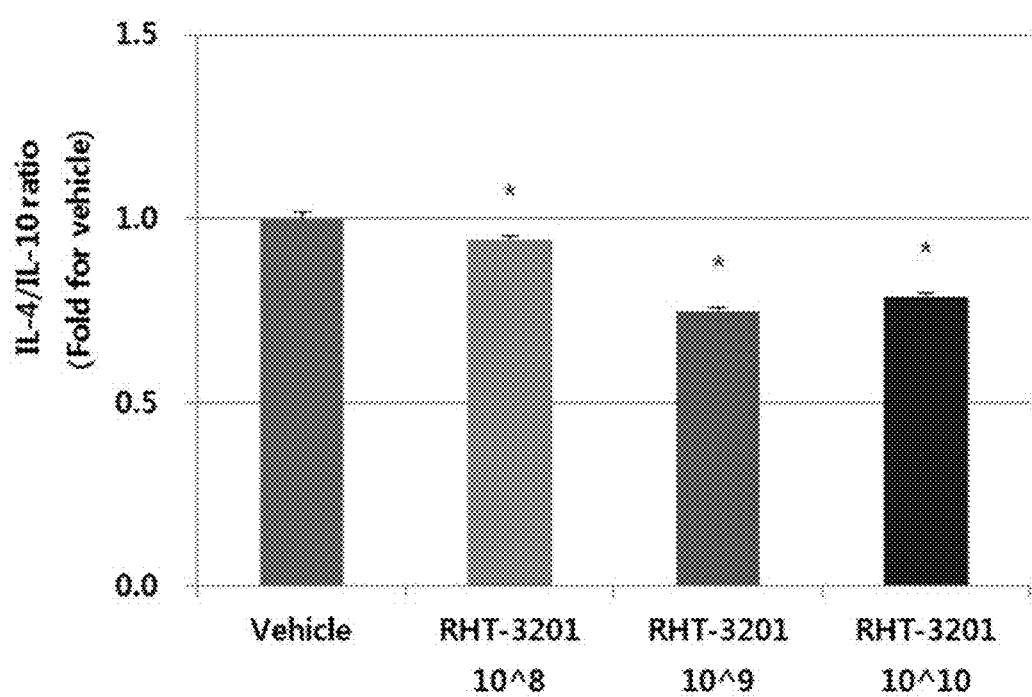
FIG. 20 illustrates the IL-4/IL-10 ratio according to the administration of RHT-3201 of the present invention in severe atopic dermatitis models.
Figure 21:
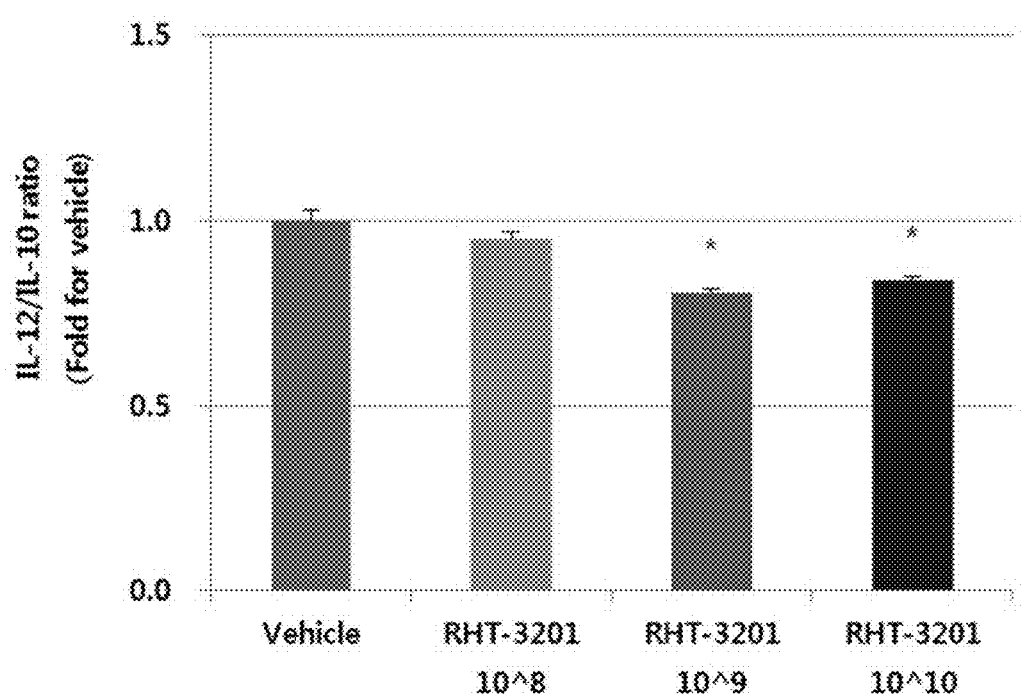
FIG. 21 illustrates the IL-12/IL-10 ratio according to the administration of RHT-3201 of the present invention in severe atopic dermatitis models.

For the comparision of action mechanism of RHT-3201 on severe atopic dermatitis, the ratio of Th1-type cytokine/Th2-type cytokine was shown for the levels of cytokines expressed in each administration group. As a result, as shown in FIG. 18, the IL-4/IFN-γ ratio was not different among the RHT-3201 administration groups compared with the vehicle group. These results are different from the Th1-type cytokine/Th2-type cytokine regulatory reaction of RHT-3201 according to the present invention on mild atopic dermatitis in Example 9, showing that RHT-3201 according to the present invention had a different action mechanism on severe atopic dermatitis. That is, it was verified that the action mechanism of RHT-3201 according to the present invention was varied according to the severity of atopic dermatitis.

For the confirmation that the action factor involved in the inhibition of regulatory T cells (Treg) as another action mechanism of RHT-3201 of the present invention on severe atopic dermatitis is cytokine IL-10, the IFN-γ/IL-10 ratio (see FIG. 19), the IL-4/IL-10 ratio (see FIG. 20), and the IL-12/IL-10 ratio (see FIG. 21) were compared and analyzed. As a result, it was verified that the ratio values were significantly decreased in the RHT-3201 administration groups of the present invention. Thus, it was shown that IL-10 is an action factor involved in the treatment of severe atopic dermatitis, and this cytokine increases the activity of Treg, thereby exhibiting the treatment effect of severe atopic dermatitis.

<10-8> Histopathological Observation

The dorsal skins of the NC/Nga mice were harvested, fixed in 10% formalin, and paraffin-embedded, and thinly cut to a thickness of 4 μm, thereby preparing a slide. Subsequently, the changes in the thickness of the epidermis and the dermis were observed by hematoxylin & eosin (H&E) staining, while the mast cells were confirmed by toluidine blue staining. The skin thickness and the number of mast cells were calculated through observation using an optical microscope of 100 and 400 magnifications.

Figure 22:
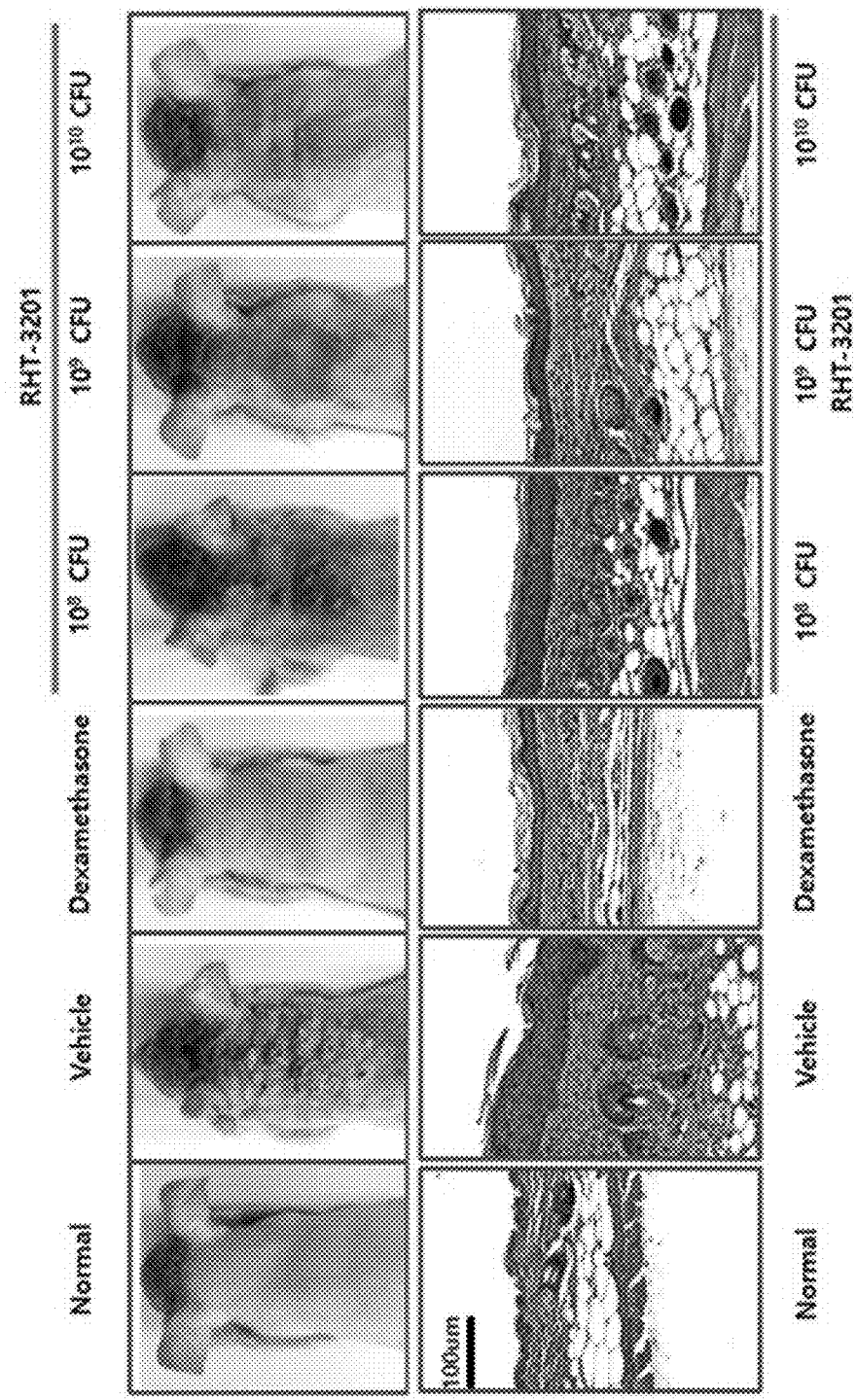
FIG. 22 illustrates macroscopic observation results of pathologic characteristics of the dorsal skin tissue according to the administration of RHT-3201 of the present invention (upper) and optical microscopic observation results of the skin tissue stained H&E stained (lower) in severe atopic dermatitis models.
Figure 23:
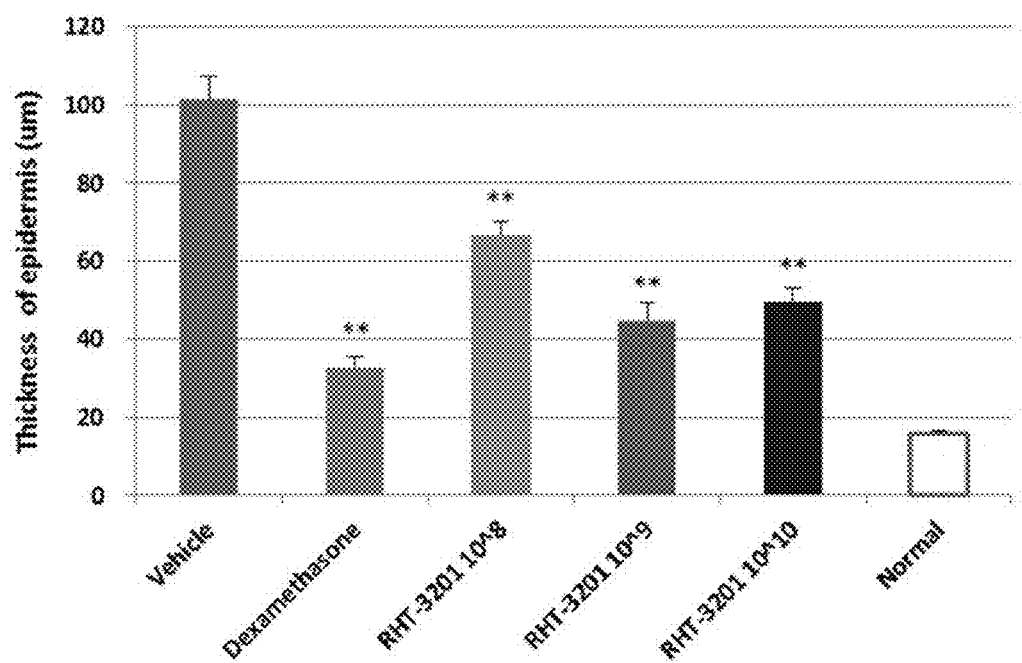
FIG. 23 illustrates the epidermis thickness of dorsal skin tissue according to the administration of RHT-3201 of the present invention in severe atopic dermatitis models.
Figure 24:
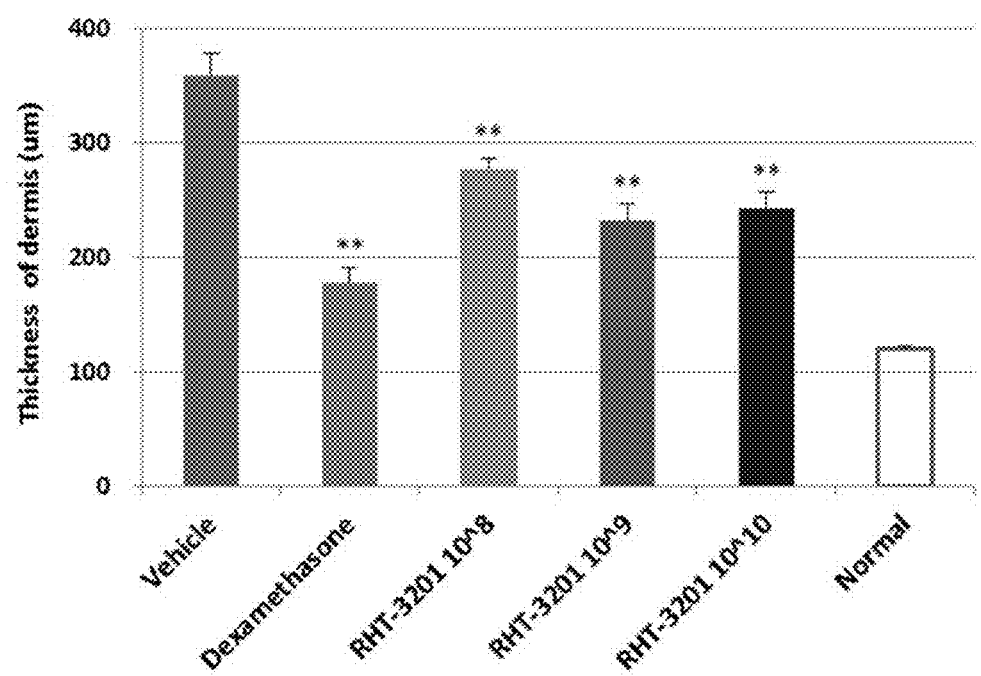
FIG. 24 illustrates the dermis thickness of dorsal skin tissue according to the administration of RHT-3201 of the present invention in severe atopic dermatitis models.

As a result of observing the dorsal skin tissues of the NC/Nga mice through H&E staining, as shown in FIG. 22, the vehicle group with atopic dermatitis induced by the exposure to dust mites showed histopathological findings of expanded thickening caused by the thickening of the epidermal layer toward the dermal layer compared with the normal group and increased infiltration of inflammatory cells. Through microscopic observation, the RHT-3201 administration groups of the present invention showed a reduced infiltration of inflammatory cells; a significant inhibition on the expandability of the epidermal thickness (see FIG. 23) and the expandability of the dermal thickness (see FIG. 24), which are observed for the induction of atopic dermatitis, in comparison with the vehicle group.

Figure 25:
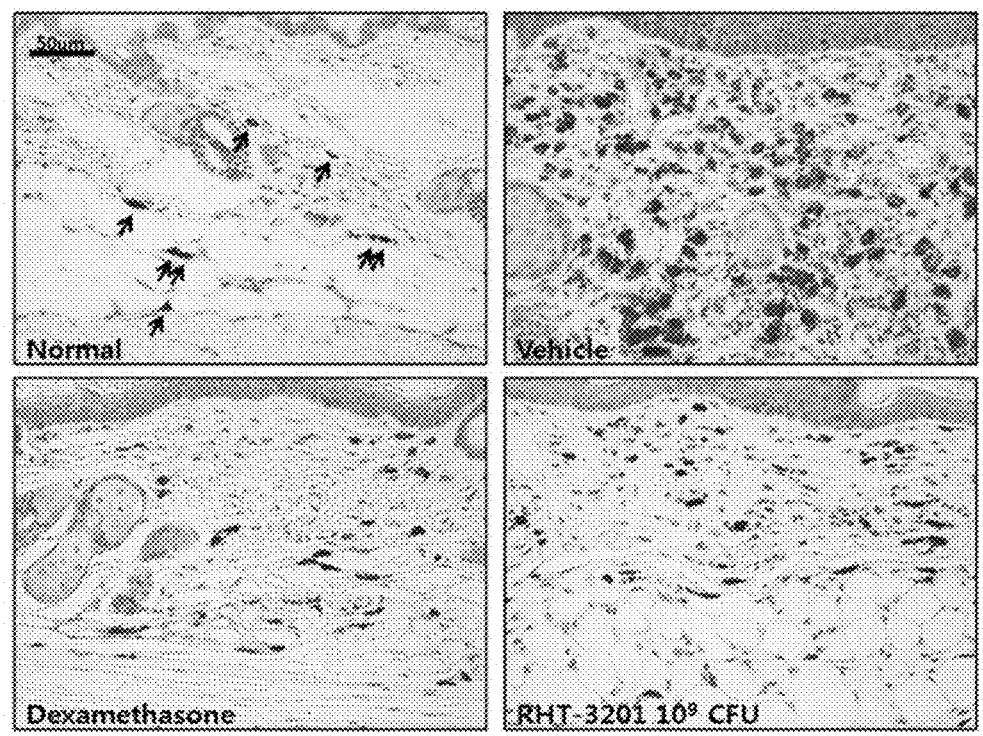
FIG. 25 illustrates results of observing the infiltration state of mast cells into the dorsal skin tissue through toluidine blue staining according to the administration of RHT-3201 of the present invention in severe atopic dermatitis models.
Figure 26:
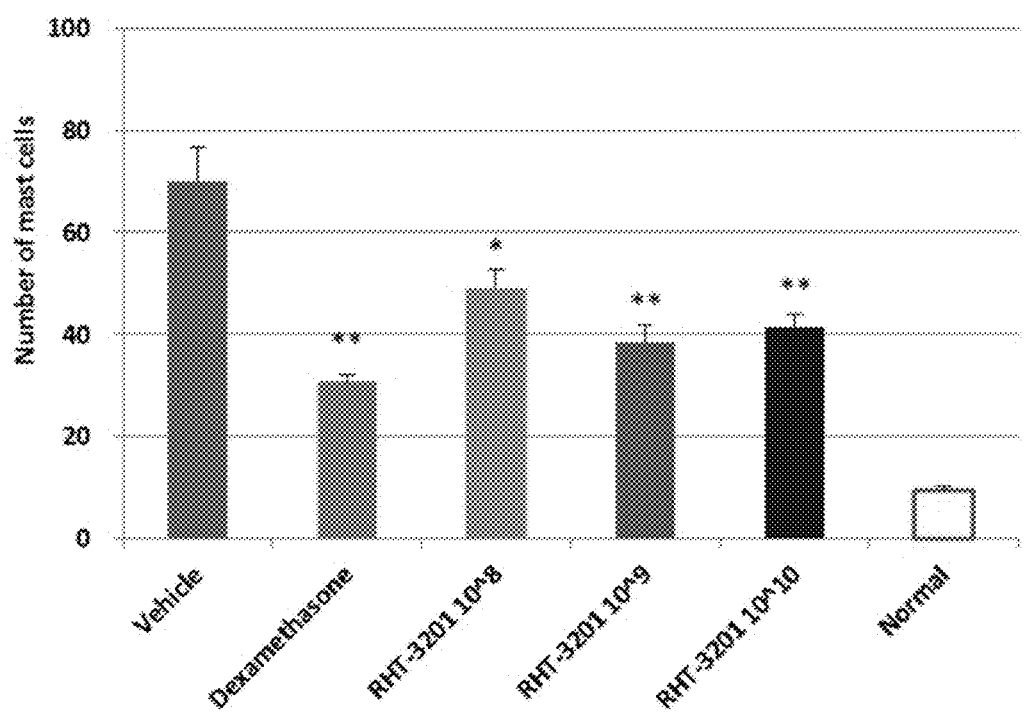
FIG. 26 illustrates the change in the number of mast cells in the dorsal skin tissue according to the administration of RHT-3201 of the present invention in severe atopic dermatitis models.

As a result of observing the dorsal skin tissues of the NC/Nga mice through toluidine blue staining, it was verified that the mast cells further infiltrated into the skin tissues in the vehicle group with atopic dermatitis induced due to the exposure to dust mites, which is an atopic dermatitis inducing antigen material, compared with the normal group (see FIG. 25). In severe atopic dermatitis, the number of mast cells is generally increased according to the period thereof. As shown in FIG. 26, it was verified that the number of mast cells was increased in the skin tissues of the mice (vehicle) exposed to dust mites for 11 weeks, whereas the number of mast cells in the severe atopic dermatitis-induced mice was significantly decreased in the groups administered with RHT-3201 for eight weeks. Therefore, RHT-3201 according to the present invention is considered to exhibit a significant effect on alleviating severe atopic dermatitis.

INDUSTRIAL APPLICABILITY

As set forth above, the present invention relates to heat-killed *Lactobacillus rhamnosus* conjugate to a polymeric polysaccharide binder, a method for preparing the same, and a use thereof. The heat-killed *Lactobacillus rhamnosus* conjugate to a polymeric polysaccharide binder of the present invention possesses an excellent therapeutic effect on atopic diseases, especially, significantly improves the adhesive competitiveness to the intestinal mucosa of conventional lactic acid bacteria preparations, and exhibits a preventing, alleviating, or treating effect on atopic dermatitis at an equivalent level to a steroid-based drug. Therefore, the present invention is highly industrial applicable.

The invention claimed is:

1. A method for preparing heat-killed *Lactobacillus rhamnosus* conjugated to a polymeric polysaccharide binder, the method comprising the steps of:
    separating a fermentation culture medium prepared by culturing *Lactobacillus rhamnosus* into bacteria and a fermentation filtrate, wherein the *Lactobacillus rhamnosus* is *Lactobacillus rhamnosus* IDCC 3201 (KCTC 10833BP);
    selecting at least one polymeric polysaccharide from the group consisting of hyaluronic acid, alginate, maltodextrin, and chitosan;
    mixing the fermentation filtrate and the at least one polymeric polysaccharide to prepare a polymeric polysaccharide binder, wherein the at least one polymeric polysaccharide is mixed with the fermentation filtrate at a ratio of 0.0001% (w/v)-10% (w/v);
    heat-killing the bacteria; and
    conjugating the polymeric polysaccharide binder to a surface of the heat-killed bacteria.

2. The method of claim 1, wherein the at least one polymeric polysaccharide is hyaluronic acid.

3. The method of claim 2, wherein the hyaluronic acid is mixed with the fermentation filtrate at a ratio of 0.0001-1% (w/v).

4. The method of claim 1, wherein the heat-killing is performed at a temperature range of 60-100° C.

5. The method of claim 1, wherein the heat-killing is performed for 10-120 minutes.

6. The method of claim 1, wherein the step of mixing further comprises a concentration process to obtain a highly concentrated polymeric polysaccharide binder.

7. The method of claim 1, wherein the at least one polymeric polysaccharide is mixed with the fermentation filtrate at a ratio of 0.0001% (w/v)-1% (w/v) in the step of mixing.

8. The method of claim 1, wherein the at least one polymeric polysaccharide is mixed with the fermentation filtrate at a ratio of 0.0001% (w/v)-0.01% (w/v) in the step of mixing.

* * * * *

UNITED STATES PATENT AND TRADEMARK OFFICE
CERTIFICATE OF CORRECTION

PATENT NO. : 10,443,033 B2
APPLICATION NO. : 15/344958
DATED : October 15, 2019
INVENTOR(S) : Lee et al.

Page 1 of 1

It is certified that error appears in the above-identified patent and that said Letters Patent is hereby corrected as shown below:

In the Specification

1. In Column 2, Line 24, delete "level or treatment" and insert -- level of treatment --, therefor.
2. In Column 3, Line 24, delete "binder" and insert -- binder. --, therefor.
3. In Column 4, Line 6, delete "binder" and insert -- binder. --, therefor.
4. In Column 10, Line 15, delete "favoring" and insert -- flavoring --, therefor.
5. In Column 10, Line 41, delete "atopy" and insert -- atopy. --, therefor.
6. In Column 14, in Table 2, Line 2, delete "Incease" and insert -- Increase --, therefor.
7. In Column 17, in Table 5, Line 1, delete "bewteen" and insert -- between --, therefor.
8. In Column 18, in Table 6, Line 3, delete "Ahesion" and insert -- Adhesion --, therefor.
9. In Column 19, in Table 9, Line 2, delete "inventio" and insert -- invention --, therefor.
10. In Column 19, in Table 9, Line 5, delete "ahesion" and insert -- adhesion --, therefor.
11. In Column 20, in Table 11, Line 5, delete "adheson" and insert -- adhesion --, therefor.
12. In Column 21, Line 57, delete "dosal" and insert -- dorsal --, therefor.
13. In Column 22, in Table 13, Line 1, delete "Sever atopic dermatitis inductin" and insert -- Severe atopic dermatitis induction --, therefor.
14. In Column 22, in Table 13, Line 2, delete "treateement" and insert -- treatment --, therefor.
15. In Column 22, in Table 13, Line 8, delete "(Postive" and insert -- (Positive --, therefor.
16. In Column 22, Line 59, delete "deceased" and insert -- decreased --, therefor.
17. In Column 23, Line 18, delete "combination number" and insert -- combination of number --, therefor.
18. In Column 24, Line 49, delete "comparision" and insert -- comparison --, therefor.

Signed and Sealed this
Second Day of June, 2020

Andrei Iancu
*Director of the United States Patent and Trademark Office*